US012383219B2

(12) United States Patent
Kovler et al.

(10) Patent No.: US 12,383,219 B2
(45) Date of Patent: Aug. 12, 2025

(54) OPTIMIZING CAMERA CALIBRATION TARGETS FOR 2D TO 3D RECONSTRUCTION

(71) Applicant: XPLAN AI Ltd., Jerusalem (IL)

(72) Inventors: Ilya Kovler, Jerusalem (IL); Hamza Abudayyeh, Jerusalem (IL); Shimon Bezalel, Jerusalem (IL); Itay Mairantz, Jerusalem (IL); Moshe Safran, Jerusalem (IL); Michal Margalit, Jerusalem (IL); Michael Librus, Jerusalem (IL); Ofer Abramov, Jerusalem (IL); Ron Soferman, Jerusalem (IL)

(73) Assignee: XPLAN AI Ltd., Jerusalem (IL)

( * ) Notice: Subject to any disclaimer, the term of this patent is extended or adjusted under 35 U.S.C. 154(b) by 0 days.

(21) Appl. No.: 18/685,915

(22) PCT Filed: Jul. 10, 2023

(86) PCT No.: PCT/IB2023/057071
§ 371 (c)(1),
(2) Date: Feb. 23, 2024

(87) PCT Pub. No.: WO2024/013642
PCT Pub. Date: Jan. 18, 2024

(65) Prior Publication Data
US 2025/0127477 A1    Apr. 24, 2025

Related U.S. Application Data

(60) Provisional application No. 63/388,014, filed on Jul. 11, 2022.

(51) Int. Cl.
*A61B 8/00* (2006.01)
*A61B 6/00* (2006.01)
(Continued)

(52) U.S. Cl.
CPC ............ *A61B 6/583* (2013.01); *A61B 6/5205* (2013.01); *G06T 7/80* (2017.01); *G06T 2207/10116* (2013.01)

(58) Field of Classification Search
CPC ............ A61B 10/00; A61B 2010/0003; A61B 2560/0223; A61B 2560/0228; A61B 6/58;
(Continued)

(56) References Cited

U.S. PATENT DOCUMENTS

| 5,005,196 A | 4/1991 | Lanza et al. |
| 10,839,557 B1 | 11/2020 | Arora et al. |

(Continued)

FOREIGN PATENT DOCUMENTS

| WO | WO-0187136 A2 * | 11/2001 | ............. A61B 34/20 |
| WO | 2021174038 A1 | 9/2021 | |

OTHER PUBLICATIONS

WO in related PCT application PCT/US2021/019963, dated Sep. 2, 2021.
(Continued)

*Primary Examiner* — Don K Wong
(74) *Attorney, Agent, or Firm* — Nathan & Associates Patent Agents Ltd.; Menachem Nathan

(57) ABSTRACT

Described herein are calibration jigs and methods used to design and fabricate calibration jigs as well as associated workflows that may be used for determining the calibration parameters used to create a 2D image of a 3D scene, wherein the calibration jig has the shape of an isosceles right semi-triangular prism and is configured to ergonomically fit an anterior-medial tibial position on a patient's leg.

14 Claims, 19 Drawing Sheets

(51) Int. Cl.
  *A61B 6/58*    (2024.01)
  *G06T 7/80*    (2017.01)

(58) Field of Classification Search
  CPC ......... A61B 6/583; A61B 6/547; A61B 6/548;
        A61B 6/545; A61B 6/5223; A61B
    6/5229; A61B 2090/364; A61B 2090/367;
      A61B 90/39; A61B 2090/3912; A61B
        2090/392; A61B 2090/3937; A61B
        2090/3945; A61B 2090/395; A61B
        2090/3966; A61B 2090/3987; A61B
              2090/3991; A61B 2090/3995
  See application file for complete search history.

(56)        References Cited

U.S. PATENT DOCUMENTS

2002/0115934 A1    8/2002  Tuke
2007/0122020 A1    5/2007  Claus et al.

OTHER PUBLICATIONS

Yavas et al. "Three-dimensional-printed marker-based augmented reality neuronavigation: a new neuronavigation technique", Aug. 2021.
Vernikouskaya et al. "3D-XGuide: open-source X-ray navigation guidance system", Oct. 2020.
International Search Report and Written Opinion in related PCT application PCT/IB2023/057071, dated Jan. 9, 2024.

\* cited by examiner

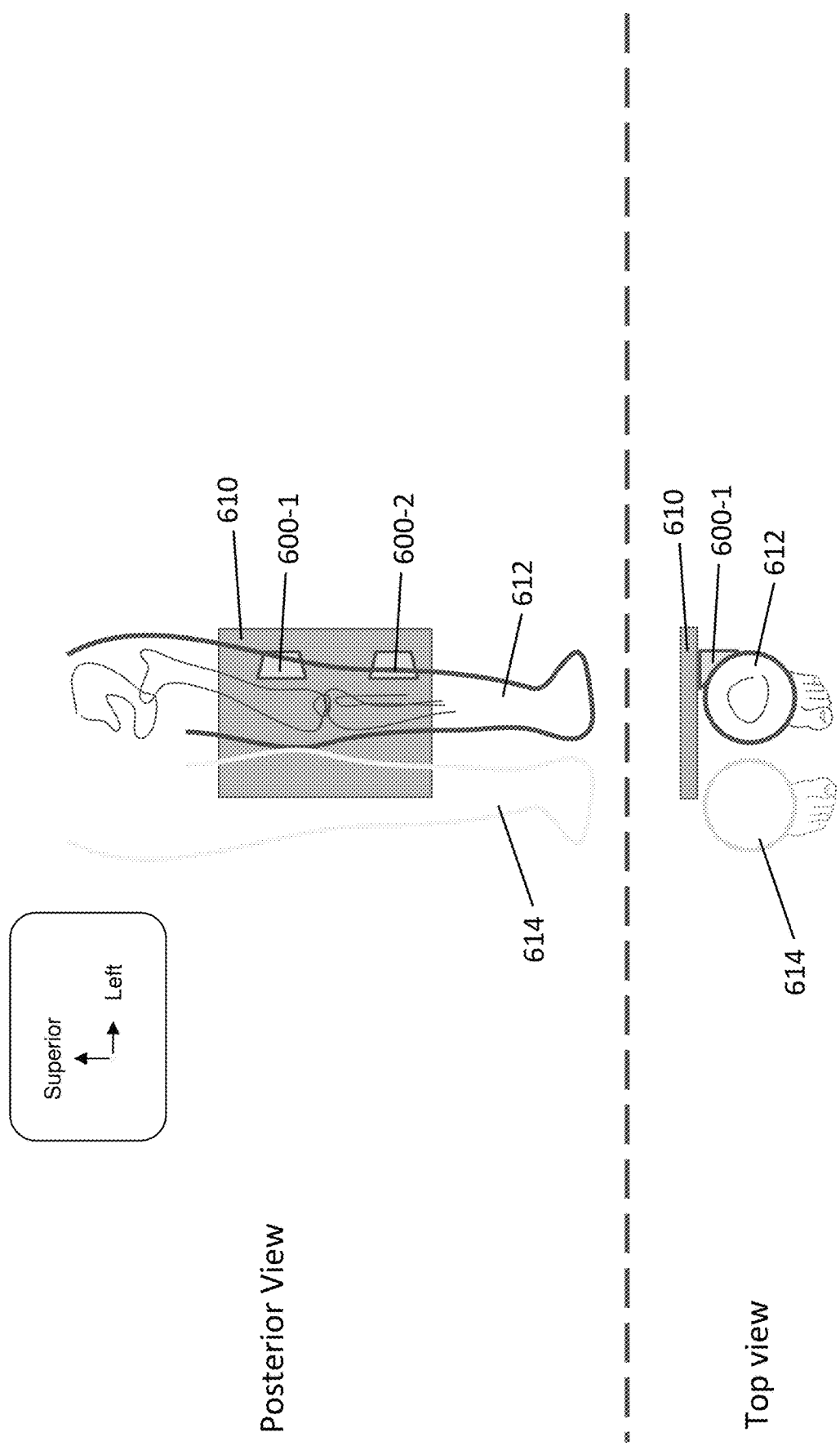

OPTIMIZING CAMERA CALIBRATION TARGETS FOR 2D TO 3D RECONSTRUCTION

CROSS-REFERENCE TO RELATED APPLICATIONS

This is a 371 application from international patent application No. PCT/IB2023/057071 filed Jul. 10, 2023, which claims the benefit of priority of U.S. Provisional Patent Application No. 63/388,014 filed Jul. 11, 2022, and the contents of which are incorporated herein by reference in its entirety.

FIELD

Subject matter disclosed herein relates generally to computer vision, and more particularly to calibration jigs (also known as "calibration targets") used in three-dimensional (3D) model reconstruction from a sparse set of two-dimensional (2D) images.

BACKGROUND 3D model creation based on a set of 2D images is one of the fundamental challenges in computer vision. This "reconstruction" is the reverse process of taking 2D images from 3D scenes. As the image forming process projects all 3D points onto a 2D plane, a single 2D image does not contain all the necessary information about the 3D scene. A general technique to overcome this issue is to take a large set of 2D images of the same scene from different angles and use this data, together with complex algorithms, to reconstruct any general 3D scene. One typical example of this is Computed Tomography (CT) where a series of X-rays (2D images) are taken while rotating the X-ray machine around the patient. This results in several hundred cross-sections of the same scene (the patient) and can be used to create a 3D model of the patient.

On the other hand, it is often difficult to reconstruct a scene based only on a few 2D images. Typically, machine-learning algorithms are used to create models based on their prior training in some narrow set of scenes. Moreover, the relative pose of the cameras used to create these images, i.e., the placement of the camera in the 3D world, is often unknown. This information, known as the camera calibration, is essential in figuring out the relation between the 2D images and the underlying 3D scene.

Camera calibration may include calculating two sets of parameters: intrinsic and extrinsic. Extrinsic parameters relate to the position and rotation of the camera in relation to the 3D scene. Intrinsic parameters, on the other hand, define internal parameters of the camera such as the focal length, pixel size, skewness, etc. In many instances the set of images are taken by the same physical camera and therefore the intrinsic parameters are fixed between different images. In such cases, the intrinsic parameters may be calibrated beforehand by using calibration meshes (such as a checkerboard mesh) that are imaged from multiple views using the same camera. These intrinsic parameters may then be used throughout while the extrinsic parameters are extracted from the images of interest.

In other cases however, either many different cameras are used or the intrinsic parameters of the same camera are constantly changing. One example of the latter is in X-ray machines where the technician changes the relative position between the source and detector for each scan and therefore changes the focal length, among other things. In such cases the calibration of both intrinsic and extrinsic parameters is necessary for each image separately.

The camera calibration process may involve using points in which both the 3D coordinates and 2D coordinates are known. Solving for the projection of the 3D points to the image points yields the calibration parameters. Calibration jigs or calibration markers may be composed of multiple objects with known 3D points. By placing these jigs or markers in the scene (or object) of interest, the camera calibration may be extracted using the resulting 2D image points.

Many examples of calibration jigs have been developed to serve specific purposes under certain circumstances. For example, several calibration jigs have been used for calibrating C-arm X-rays. Here two assumptions are implicitly made: one is that the intrinsic parameters of the camera are not changing, and the other is that the 3D object of interest (the patient here) is not moving between frames, both of which are valid for C-arm machines but do not generalize to other situations. In particular, with standard X-rays both the patient and apparatus move between frames. Therefore, in addition for the need to calibrate each image completely independently from the other, there is also a need that the calibration jig be attached to the 3D object of interest in a certain manner in order to account for the object's movement. This also introduces constraints that must be met by the calibration jig design. In addition, the calibration error of the jig, i.e., how well the calibration from this jig reproduces the actual camera calibration, is usually not accounted for during design.

Therefore, there is a need for a general optimization procedure that can produce a calibration jig with minimal calibration error within predefined design constraints. There is also a need for a calibration jig that can be positioned stably on the patient, in order to minimize the effects of the patient's movement between acquiring multiple X-ray images including jig positioning relative to the bone of interest. In addition, there is a need for related workflows and procedures to ensure that it is easy and convenient for X-ray technicians to position the jig in a desired anatomical location.

SUMMARY

In various embodiments there are provided calibration jigs (targets) and methods used to design and fabricate calibration jigs as well as associated workflows that may be used for determining the calibration parameters used to create a 2D image of a 3D scene. For simplicity, a calibration jig disclosed herein may be referred to also as just "jig". The methods of jig design may be based on optimizing the 3D position of jig components under some design error constraints and assuming certain views. Using 3D jig component position information with a series of algorithms may enable performing of multiple tasks in the field of computer vision including but not limited to 2D to 3D reconstruction.

The design and fabrication of a calibration jig disclosed herein may include one or more of the following factors:
 Calculating a calibration error based on multiple metrics, including but not limited to overlap error, reprojection error, and Euclidean distance.
 Adding external errors to this calibration error calculation, including but not limited to fabrication errors, image blurring effects, image resolution, etc.
 Designing a jig enclosure to have a specific shape that may fit a specific use case. For example, the enclosure may have a triangular structure to aid placement in a desired location such as the anterior-medial position, and/or a curved back face to fit snugly on a shin bone.

Workflow optimization-mandating jig placement in a particular anatomical location such as to minimize jig movement relative to the anatomy of interest even under conditions in which the patient is moving between the X-ray acquisitions. For example, placement of the jig on the anterior-medial portion of the tibia (shin bone) such that the jig is tightly coupled to the tibia bone even when the patient moves from an Anterior-Posterior (AP) to a Medial-Lateral (ML) position.

Using an optimization algorithm that may minimize the calibration error by moving the jig components within the geometric limitations of the jig, to fit a specific use case where images are taken from certain views. This optimization may be carried out by any suitable algorithm, including but not limited to classical algorithms (such as gradient descent), metaheuristics (such as particle-swarm optimization), or machine learning algorithms.

Using ad hoc assumptions to overcome the intrinsic limitations of the calibration process such as biases in the jig position and angles.

Automatic detection of the jig components within a 2D image and performing the calibration based on this detection.

Creating composite targets based on multiple jigs and/or alignment components for multiple use cases, including but not limited to: fixation of the constituents of the 3D model of interest in the scene between different views to prevent unwanted movements including bending; fixation of the 3D model of interest with respect to some frame of reference; stitching 2D images together based on the knowledge of the composite jig; combining multiple 3D models which were created based on different 2D images; and comparing between 3D models which were created based on different 2D images and finding points of interest on these models.

Consistent with some disclosed embodiments a method for capturing an X-ray image of a patient's leg includes: attaching a first calibration jig to the patient's leg in an anterior-medial tibial or posterior-lateral tibial position, wherein the first calibration jig has an isosceles right semi-triangular prism shape; and verifying that the first calibration jig is in the anterior-medial tibial or posterior-lateral tibial position for the capturing of an X-ray image.

In some embodiments the verifying includes positioning an isosceles right side of the first calibration jig against a detector of a device used for the capturing the X-ray image. In some embodiments the method further includes capturing an X-ray image in an anterior-posterior (AP) projection and an X-ray image in a lateral projection.

In some embodiments a base of the semi-triangular prism is curved to ergonomically fit against the patient's leg. In some embodiments a base of the semi-triangular prism is curved to ergonomically fit an anterior-medial tibial position on the patient's leg.

In some embodiments the first calibration jig includes an enclosure and a plurality of components housed inside the enclosure. In some embodiments a positioning of the components within the enclosure is optimized to minimise an error metric selected from the group consisting of a reprojection error, an overlap error, and a 3D Euclidean distance error. In some embodiments the components include spheres having different radii.

In some embodiments the method further includes: providing 2D X-ray images of the first calibration jig attached to the patient's leg, wherein the components have known 3D coordinates within the first calibration jig; determining a projection matrix from a projection of the known 3D coordinates to 2D image coordinates of the components captured in the 2D X-ray images; and decomposing the projection matrix into intrinsic and extrinsic parameter matrices and using the intrinsic and extrinsic parameter matrices for 3D reconstruction from the 2D X-ray images, wherein the extrinsic parameters relate to the position and rotation of an X-ray camera that captured the 2D X-ray images in relation to the 3D coordinates, and wherein the intrinsic parameters define internal parameters of the X-ray camera.

In some embodiments the method further includes positioning a second calibration jig in a femoral position on the patient's leg.

Consistent with some disclosed embodiments a calibration jig includes: an enclosure; and a plurality of components housed inside the enclosure, wherein the enclosure has an isosceles right semi-triangular prism shape, and wherein the calibration jig is configured to be imaged by an X-ray imager.

In some embodiments a base of the semi-triangular prism is curved to ergonomically fit against a patient's leg. In some embodiments a base of the semi-triangular prism is curved to ergonomically fit an anterior-medial tibial position on a patient's leg.

In some embodiments the components are not radio-opaque. In some embodiments the components are held in fixed positions within the enclosure. In some embodiments the calibration jig further includes a rigid adjustable attachment bar attached to the calibration jig and to a secondary calibration jig having the same shape as the calibration jig.

Consistent with some disclosed embodiments a method includes: providing enclosure bounds for an enclosure of an X-ray calibration jig; and optimizing the positioning of jig components within the enclosure bounds to minimise an error metric selected from the group consisting of a reprojection error, an overlap error, and a 3D Euclidean distance error.

In some embodiments the inputs to the optimizing include at least one of: the error metric, the enclosure bounds, sets of projection matrices for 2D views of interest, a number and size of the components, a shape of the components, a minimal allowed distance between the components, spatial constraints on the component placement, and/or initial coordinates of the components within the enclosure. In some embodiments the initial coordinates of the components within the enclosure may be random, or based on user designs.

Consistent with some disclosed embodiments a method includes: providing at least two X-ray images of a dual calibration jig attached to a patient, wherein the dual-jig includes two enclosures joined by an attachment bar, wherein each of the two enclosures includes components therein having known 3D coordinates within the enclosures, and wherein each of the at least two X-ray images captures one of the two enclosures; determining a position of the components in the X-ray images; and stitching together the at least two X-ray images based on the known 3D coordinates and the determined positions.

In some embodiments the attachment bar is rigid. In some embodiments the attachment bar is adjustable for adjusting the distance between the enclosures. In some embodiments the attachment bar includes a radio-opaque indicator used to determine the relative positions of the two enclosures. In some embodiments the attachment bar includes a radio-opaque indicator used to determine the length of the adjustable attachment bar.

In some embodiments the at least two X-ray images contain a hip joint region and a knee joint region. In some embodiments the at least two X-ray images contain a hip joint region and an ankle joint region. In some embodiments the image stitching is used to determine a mechanical axis or axes of a patient's femur, tibia, and/or whole leg.

Consistent with some disclosed embodiments a computer program product includes: a non-transitory tangible storage medium readable by a processing circuit and storing instructions for execution by the processing circuit for performing a method including: providing enclosure bounds for an enclosure of an X-ray calibration jig; and optimizing the positioning of jig components within the enclosure bounds to minimise an error metric selected from the group consisting of a reprojection error, an overlap error, and a 3D Euclidean distance error.

In some embodiments the inputs to the optimizing include at least one of: the error metric, the enclosure bounds, sets of projection matrices for 2D views of interest, a number and size of the components, a shape of the components, a minimal allowed distance between the components, spatial constraints on the component placement, and/or initial coordinates of the components within the enclosure. In some embodiments the initial coordinates of the components within the enclosure may be random, or based on user designs.

Consistent with some disclosed embodiments a computer system includes a hardware processor configurable to perform a method including: providing enclosure bounds for an enclosure of an X-ray calibration jig; and optimizing the positioning of jig components within the enclosure bounds to minimize an error metric selected from the group consisting of a reprojection error, an overlap error, and a 3D Euclidean distance error. In some embodiments the inputs to the optimizing include at least one of: the error metric, the enclosure bounds, sets of projection matrices for 2D views of interest, a number and size of the components, a shape of the components, a minimal allowed distance between the components, spatial constraints on the component placement, and/or initial coordinates of the components within the enclosure. In some embodiments the initial coordinates of the components within the enclosure may be random, or based on user designs.

Consistent with some disclosed embodiments a computer system includes a hardware processor configurable to perform a method including: determining a position of components in at least two X-ray images of a dual calibration jig attached to a patient; and stitching together the at least two X-ray images based on 3D coordinates of the components in the dual calibration jig and the determined positions.

Consistent with some disclosed embodiments a computer program product includes: a non-transitory tangible storage medium readable by a processing circuit and storing instructions for execution by the processing circuit for performing a method including: determining a position of components in at least two X-ray images of a dual calibration jig attached to a patient; and stitching together the at least two X-ray images based on 3D coordinates of the components in the dual calibration jig and the determined positions.

This Summary is provided to introduce a selection of concepts in a simplified form that may be further described in the Detailed Description below. It may be understood that this Summary is not intended to identify key features or essential features of the disclosure, nor is it intended to be used to limit the scope of the disclosure. The details of one or more embodiments disclosed herein may be set forth in the accompanying drawings and the description below. Other features will be apparent from the description and drawings, and from the claims.

BRIEF DESCRIPTION OF THE DRAWINGS

Non-limiting embodiments disclosed herein are described below with reference to figures attached hereto that are listed following this paragraph. identical structures, elements or parts that appear in more than one figure are generally labeled with the same numeral in all the figures in which they appear. When similar reference numerals are shown, corresponding description(s) are not repeated, and the interested reader is referred to the previously discussed figure(s) for a description of the like element(s). The drawings and descriptions are meant to illuminate and clarify embodiments disclosed herein, but should not be considered limiting in any way. In particular, variations and modifications apparent to those skilled in the art may be considered without departing from the claimed scope.

FIGS. 6A-6D are illustrative drawings showing exemplary placement of calibration jigs and the general setup within an imager according to some implementations;

DETAILED DESCRIPTION

Disclosed embodiments include methods, systems, devices, and computer-readable media. for providing a technical solution to the challenging technical problem of optimization and use of image calibration jigs, and relate to a system for providing optimization of image calibration jigs with the system having at least one processor (e.g., processor, processing circuit or other processing structure described herein). For ease of discussion, example methods are described below with the understanding that aspects of the example methods apply equally to systems, devices, and computer-readable media. For example, some aspects of such methods may be implemented by a computing device or software running thereon. The computing device may include at least one processor (e.g., a CPU, GPU, DSP, FPGA, ASIC, or any circuitry for performing logical operations on input data) to perform the example methods. Other aspects of such methods may be implemented over a network (e.g., a wired network, a wireless network, or both).

As another example, some aspects of such methods may be implemented as operations or program codes in a non-transitory computer-readable medium. The operations or program codes may be executed by at least one processor. Non-transitory computer readable media, as described herein, may be implemented as any combination of hardware, firmware, software, or any medium capable of storing data that is readable by any computing device with a processor for performing methods or operations represented by the stored data. In a broadest sense, the example methods are not limited to particular physical or electronic instrumentalities, but rather may be accomplished using many differing instrumentalities.

Figure 1B:
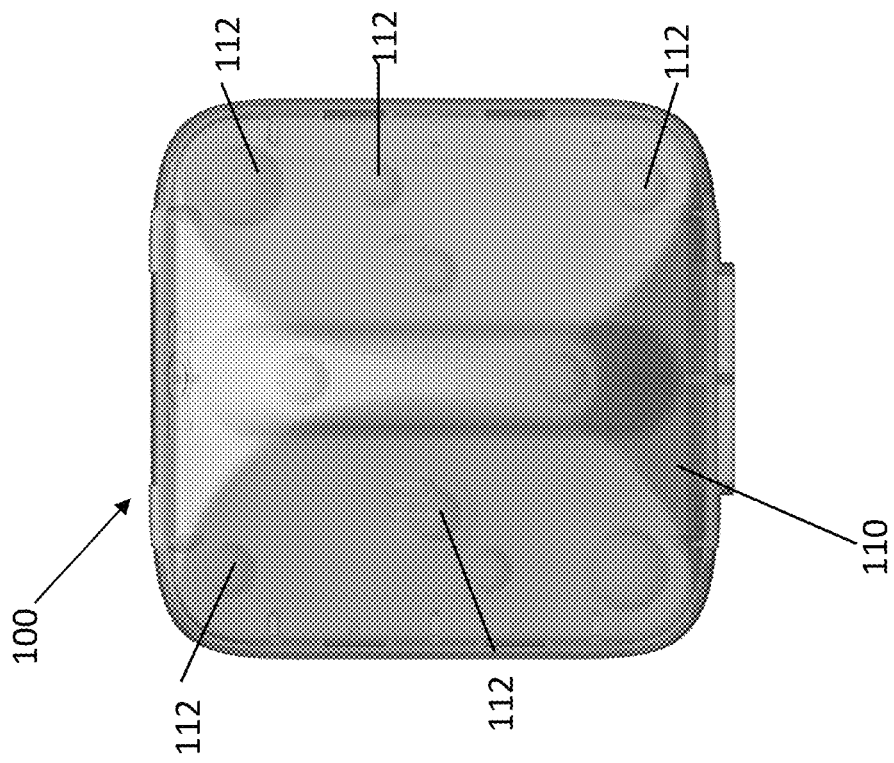
FIGS. 1A-1C show an exemplary calibration jig according to some implementations.
Figure 1A:
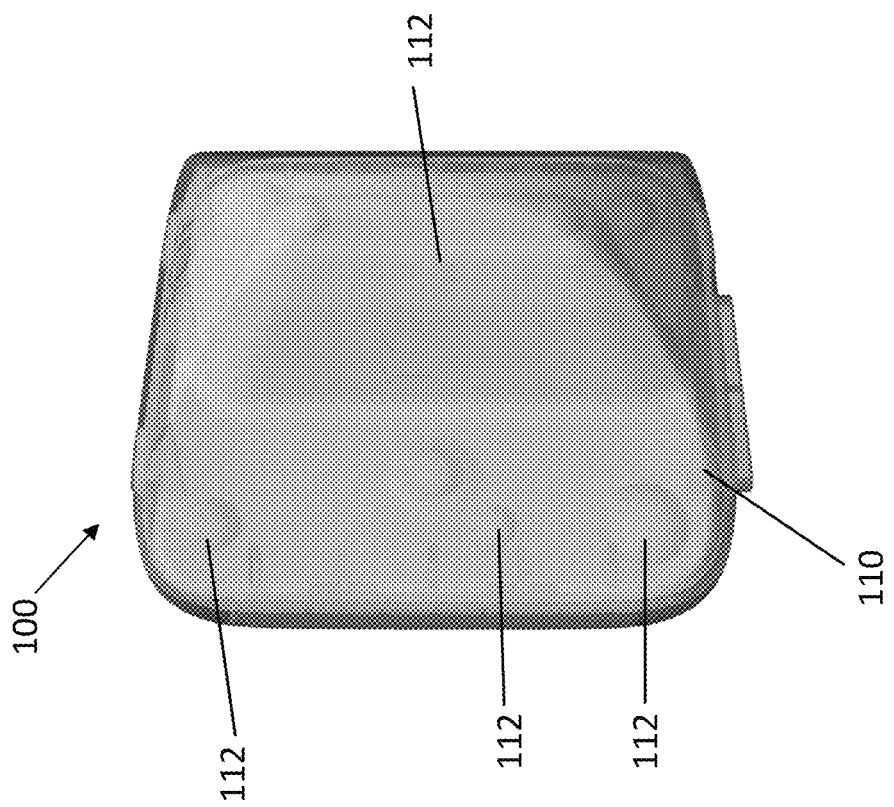
Figure 1C:
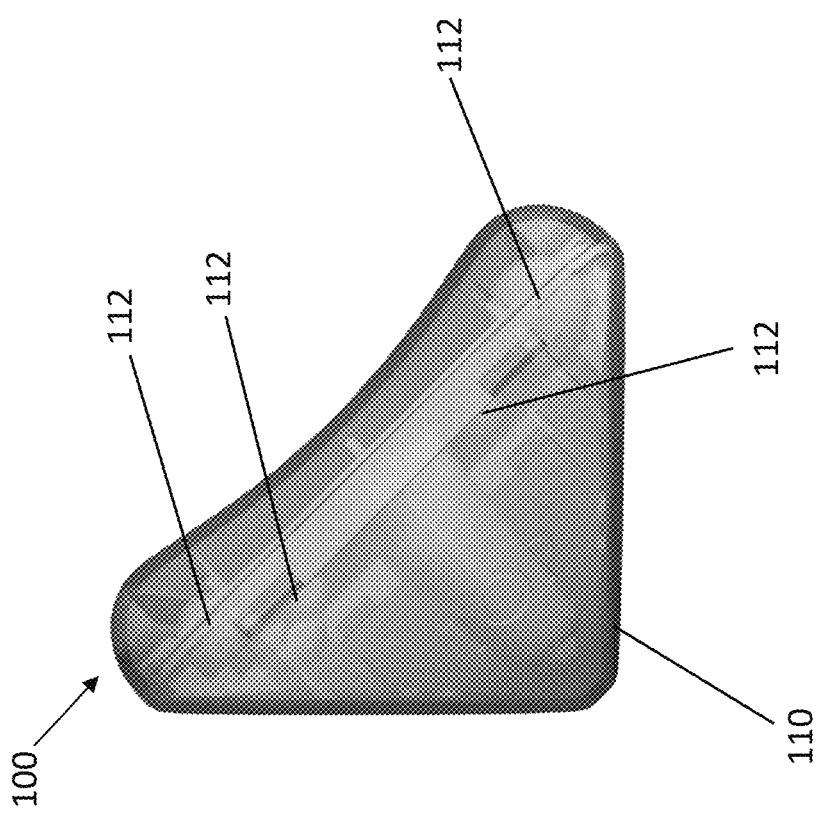

FIGS. 1A-1C show an exemplary calibration jig numbered 100 according to some embodiments disclosed herein. FIGS. 1A and 1B show alternative side views and FIG. 1C shows a plan view of jig 100. In some embodiments, jig 100 may include an outer enclosure 110 and multiple inner components 112. Components 112 may be arranged in a unique arrangement such that when viewed by a camera from different camera views, jig 100 may appear different, and the unique appearance for each camera view may enable calibration of the camera.

In some embodiments, components 112 may include multiple spheres. In some embodiments, each of components 112 may have different sizes or may be a combination of components of different sizes with components of substantially the same size. In some embodiments, components are substantially not radio-opaque. In some embodiments, enclosure 110 is substantially radio-opaque. In some embodiments, enclosure 110 may be formed from a plastic material. In some embodiments, components 112 may be held in fixed positions within enclosure 110.

In some embodiments, in order to maximize accuracy and reduce the effect of artifacts, the form of enclosure 110 may be carefully designed in terms of thickness and density, as well as shape. For example, structural planes that are perpendicular to viewing angles in an X-ray may cause a high intensity line in the corresponding X-ray image and therefore, in some embodiments, enclosure 110 may include rounded edges so as to produce fewer high-intensity artifacts during imaging. In some embodiments, enclosure 110 may be shaped to fit onto a specific anatomical position of a patient to ensure substantially consistent anatomical positioning of jig 100 on multiple patients.

Similarly, it is preferable not to hold components 112 in their respective positions using internal plastic supports, as these supports may lead to artifacts in an X-ray image. Therefore, in some embodiments, a vacuum-packed low-density polyethylene may be used to position and hold in place components 112 in a unique 3D arrangement within enclosure 110.

Figure 1D:
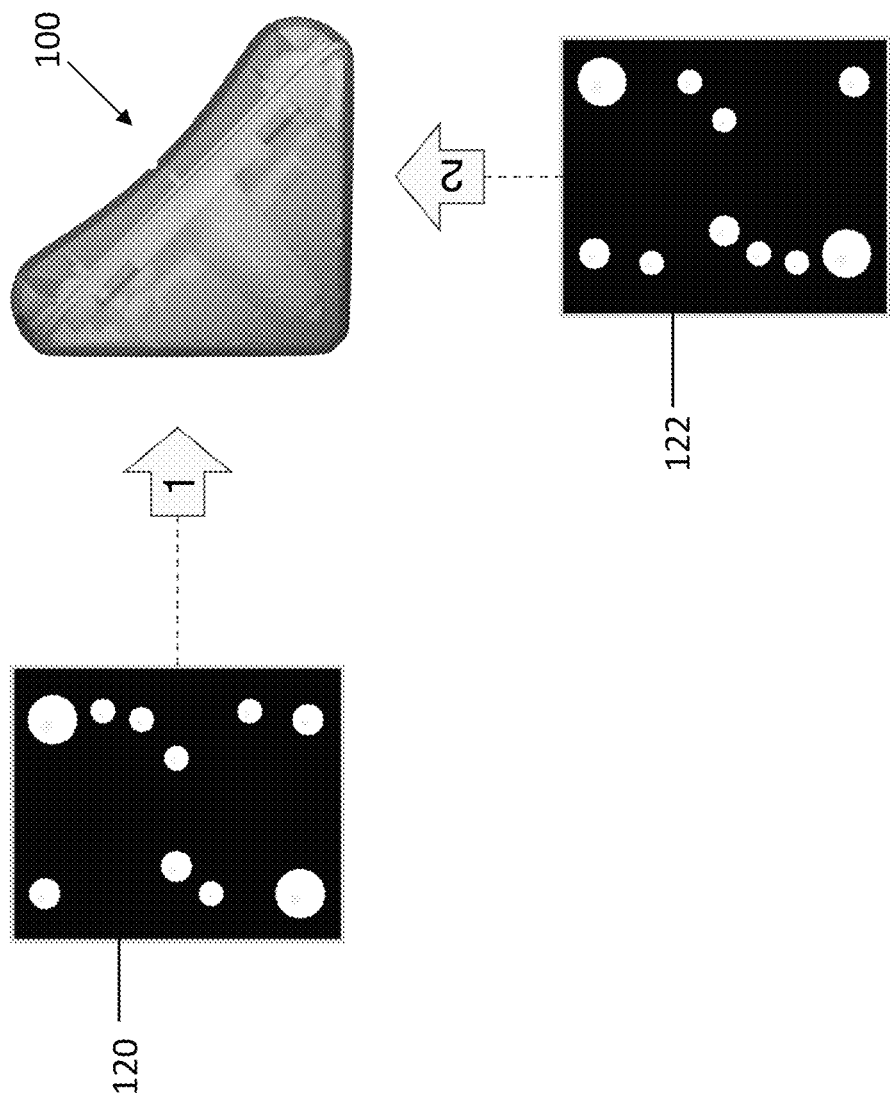
FIG. 1D shows illustrative X-ray images of a calibration jig captured by a camera from different viewing angles according to some implementations.

FIG. 1D shows illustrative X-ray images of jig 100 captured by a camera from different viewing angles (1) and (2). As shown in FIG. 1D, the imaged pattern of components 112 will be different in images 120 and 122 taken of jig 100 from the different viewing angles (1) and (2). As above, the unique appearance for each camera view may enable calibration of the camera. An optimization algorithm (such as described in process 200 below) may maximize the positions of components 112 within enclosure 110 both in a base-plane and by placing two components 112 at an apex of a triangular prism. As can be seen in images 120 and 122, this configuration may minimize the chance for overlap in the 2D views of interest.

Figure 2A:
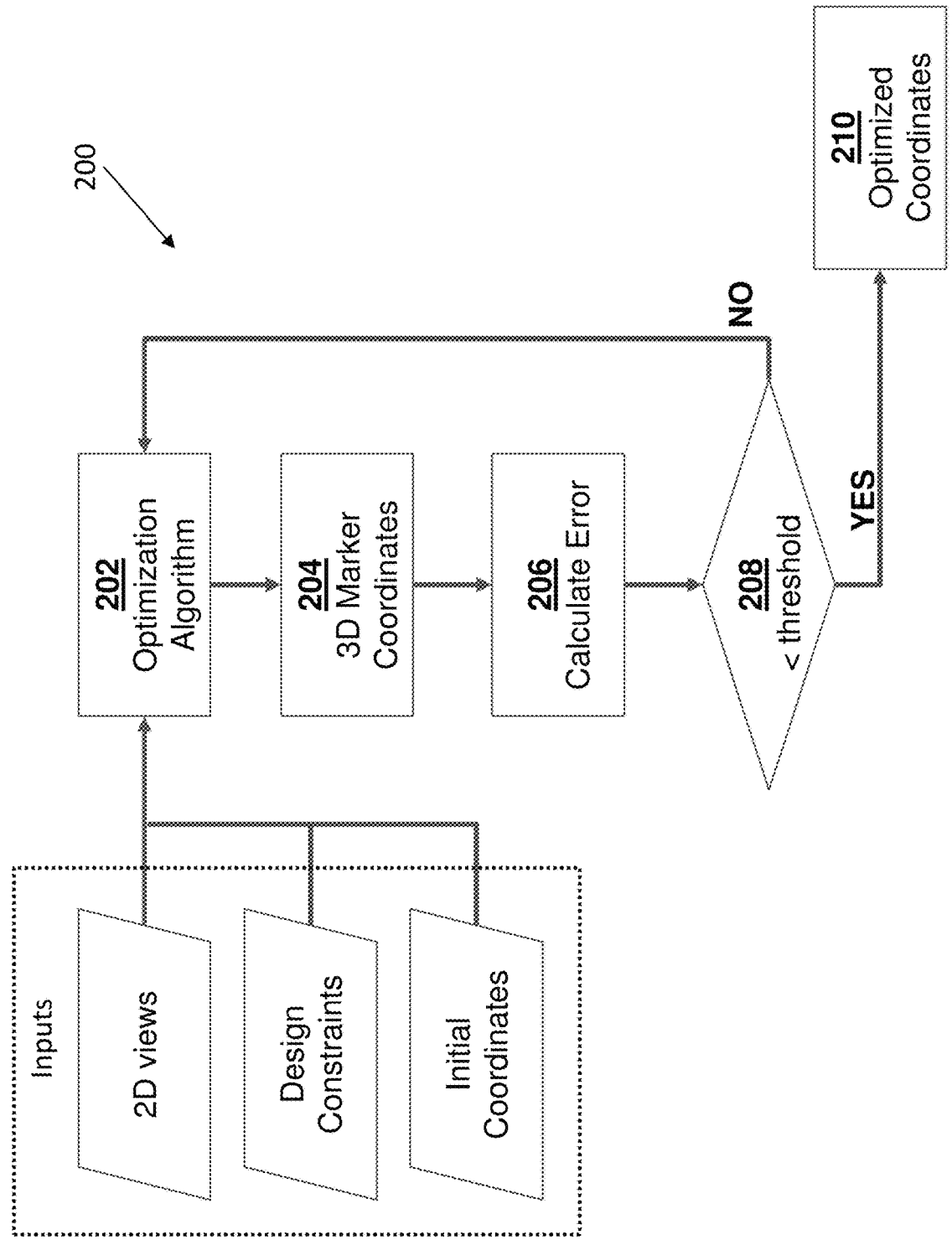
FIG. 2A shows a flowchart of process for calibration jig design optimization according to some implementations.

FIG. 2A shows a flowchart of process numbered 200 for jig optimization in accordance with embodiments disclosed herein. Process 200 may be implemented in a system 700 as described below for optimizing the positioning of jig components such as in jigs 100, 400, 500, and 600 described herein. A non-transitory computer readable medium may contain instructions (such as but not limited to the described optimization algorithm) which, when executed by at least one processor, perform the method and operations described at each of the steps in process 200. The non-transitory computer readable medium and at least one processor may correspond to one or more of jig optimization engine 714, controller 712, and memory 720 of calibration jig server 710 as described herein, and/or other components of calibration jig server 710 that may be controlled by controller 712. Process 200 running on calibration jig server 710 may make use of machine learning processes as defined herein.

In some embodiments, the inputs to process 200 may include error metrics, sets of projection matrices for the 2D views of interest, design constraints such as jig enclosure bounds, number and size of components, shape of components, minimal allowed distance between components, spatial constraints on component placement due to the properties of the plastic supports for the components, and initial coordinates of the jig components within the enclosure that may be random or based on user designs.

In step 202, these inputs may be provided to an optimization algorithm for optimizing the positioning of the jig components. In step 204, the optimization algorithm provides a set of 3D coordinates, and in step 206 an optimization error is calculated. In decision step 208, if the optimization error is below a predefined threshold, then the optimization is halted and the resulting coordinates are the optimized coordinates for the jig components. If the optimization error is above the predefined threshold, then steps 202-206 are repeated for another iteration of the optimization process.

Figures 2B, 2C, 2D:
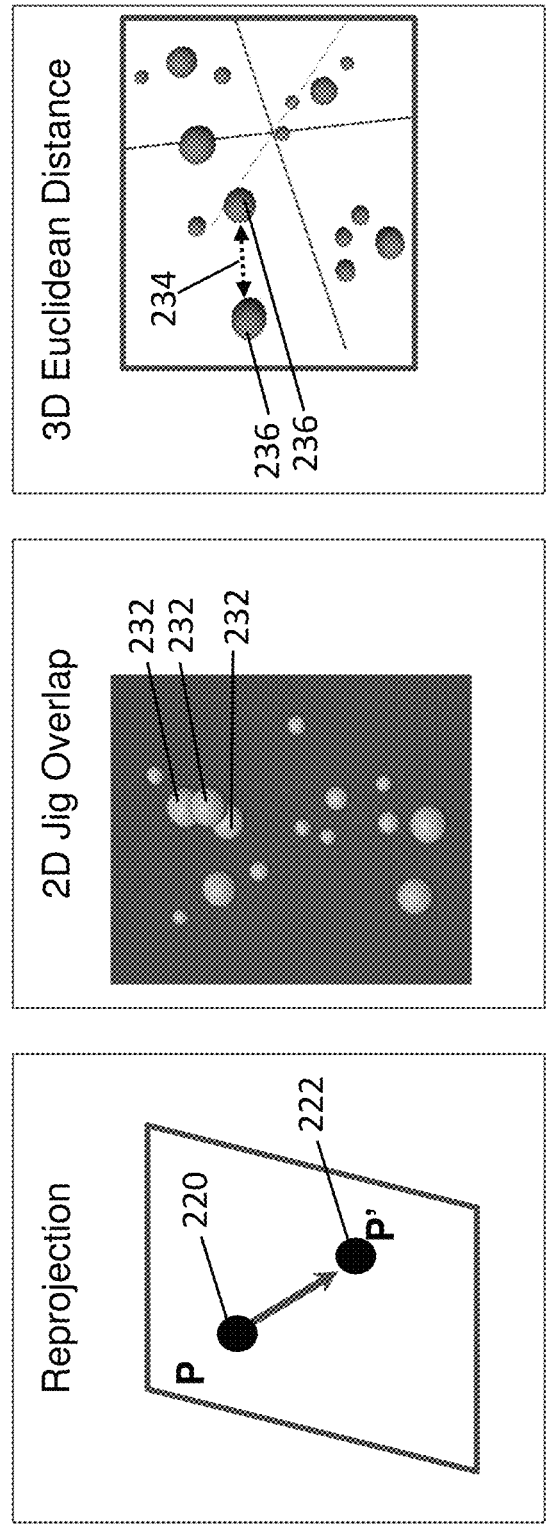
FIG. 2B-2D show illustrations of optimizations in a jig optimization process according to some implementations.

In some embodiments, one or more error metrics may be used in the optimization algorithm to optimize the jig component positions under some set of external constraints. FIGS. 2B-2D illustrates some of the error metrics that may be minimized including a reprojection error, overlap error, and 3D Euclidean distance error.

FIG. 2B is an illustration of a reprojection error showing a component location 220 as detected in the original 2D image and a reprojected location 222 of the component in the 2D image after performing calibration and applying the resulting projection metric to the 3D component location. A reprojection error may be determined based on a generated set of sample points in a 3D space. These sample points, in addition to the 3D coordinates of the jig components, may be projected to a variety of 2D image planes by using a set of projective parameters that represent the typical use case. The projection of the sample points can be called the "true image points". The 2D jig image points may then be moved slightly around using random Gaussian blurring to mimic detection and pixelization errors. These points may then be used for camera calibration. The resulting calibration may then be used to reproject the sample points resulting in "reprojected image points". The Euclidean distance between the true and reprojected image points may then be used as an error metric representing the calibration error for that specific jig design. This error metric takes into account the accuracy of the jig in producing calibrations for certain 2D views and certain 3D sample points. These views and sample points can be tailored to a specific application of interest.

FIG. 2C illustrates a component overlap error where jig components (represented by spheres 232) overlap for a chosen viewing angle. An overlap error may be determined by using a set of projective parameters that represent the typical use case with the 3D jig components projected onto different 2D views. The number of overlaps between the jig components may be counted and used to represent the overlap error. This error metric seeks to prevent overlaps of components in the 2D views of interest in order to minimize any 2D detection and matching errors.

FIG. 2D illustrates a 3D Euclidean distance error showing the 3D distance 234 between two of the components (spheres 236), given some 3D jig design (here shown with spherical components). The calibration error of a jig at a certain distance may be directly influenced by the size of the jig along that direction. It is therefore important to maximize the distribution of the jig components along all directions. This error metric aims to maximize the distance between jig components in 3D and therefore force the components to spread within the allowed constraints.

Figure 2G:
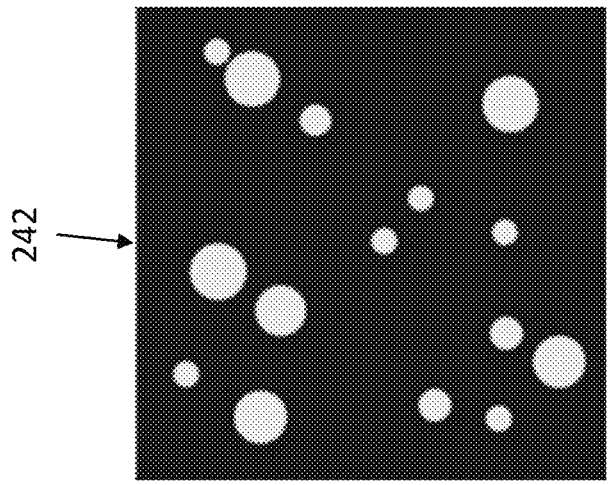
FIGS. 2F and 2G show projections of the 3D arrangement of FIG. 2E according to some implementations.
Figure 2F:
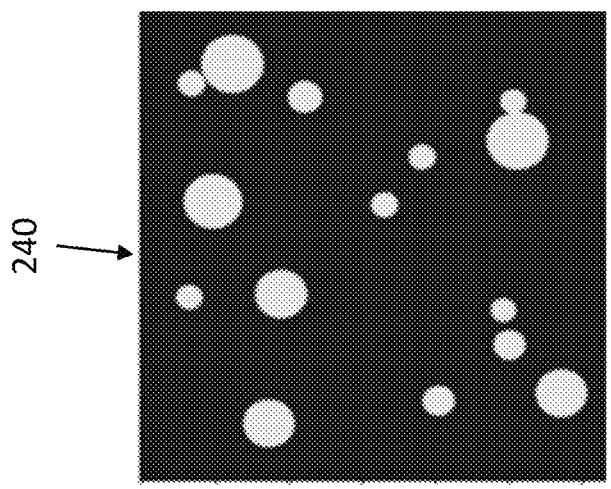
Figure 2E:
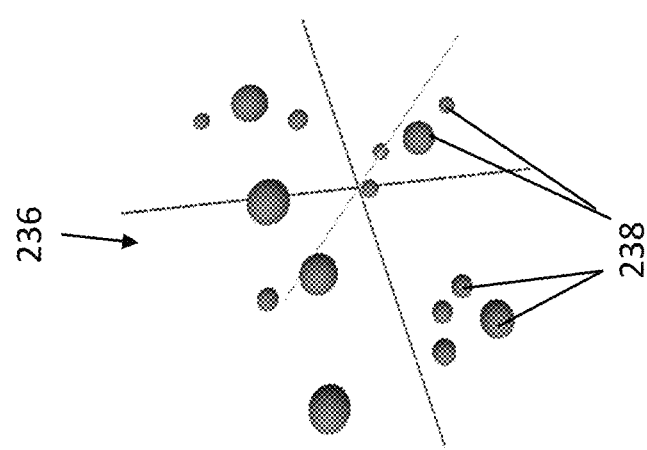
FIG. 2E shows an exemplary 3D arrangement of jig components represented by spheres according to some implementations.

FIG. 2E shows an exemplary 3D arrangement 236 of jig components represented by spheres 238 according to some implementations. In the embodiment of FIG. 2E, the 3D design of the jig components includes several spheres 238 of different radii positioned following use of an optimization algorithm such as process 200 described above. Jigs 100, 400 or 500 (see below) may be constructed including jig components 112 positioned in such an arrangement.

FIGS. 2F and 2G show illustrative projections 240 and 242 of the 3D arrangement of FIG. 2E from an X-ray camera having a detector parallel to the XZ plane (FIG. 2F) and a camera having a detector parallel to the YZ plane (FIG. 2G).

Figure 3A:
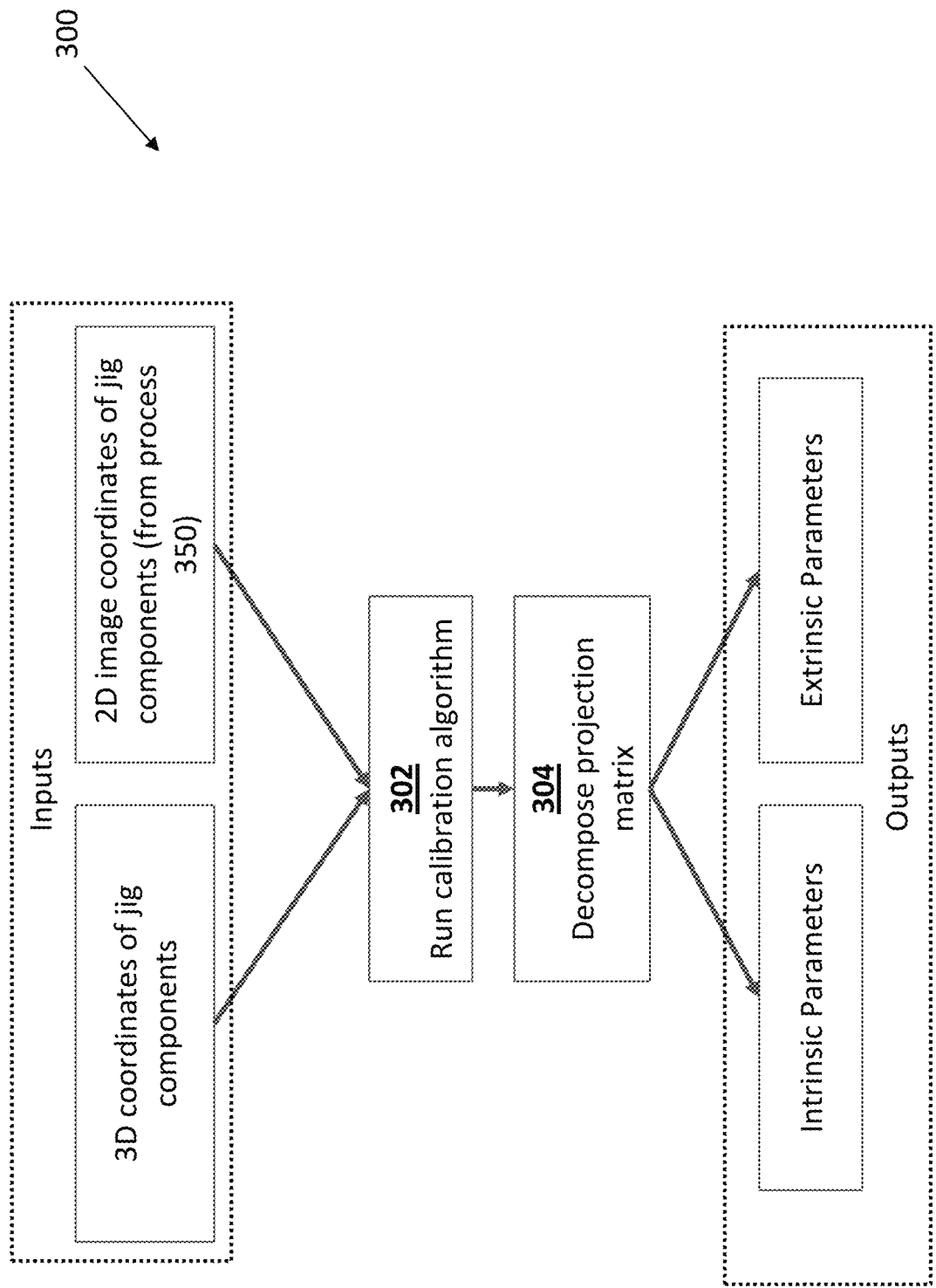
FIGS. 3A and 3B show flow diagrams of camera calibration processes 300 and 350 using a calibration jig according to some implementations.
Figure 3B:
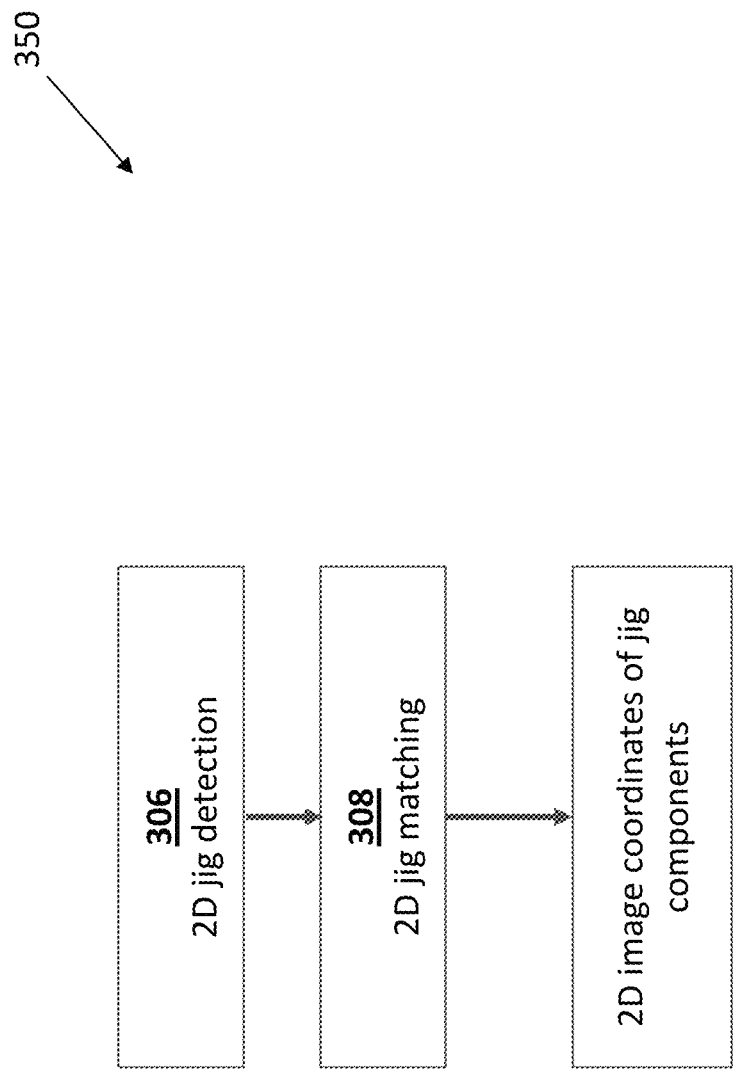

FIGS. 3A and 3B show flow diagrams of camera calibration processes 300 and 350 using a calibration jig in accordance with embodiments disclosed herein. Processes 300 and 350 may be implemented in a system 700 as described herein for calibrating cameras (such as but not limited to X-ray cameras) that capture 2D images of jigs such as jigs 100, 400, 500 and 600 described herein. A non-transitory computer readable medium may contain instructions which, when executed by at least one processor, perform the method and operations described at each of the steps in process 300 (such as but not limited to the described calibration algorithms). The non-transitory computer readable medium and the at least one processor may correspond to one or more of a calibration engine 716, a controller 712, and a memory 720 of a calibration jig server 710 (see below), and/or other components of calibration jig server 710 that may be controlled by controller 712. Process 300 running on calibration jig server 710 may make use of machine learning processes as defined herein.

Calibration process 300 may require two inputs: the 3D coordinates of the components of the jig being imaged, and the 2D coordinates of the jig components (such as components 112) in the image frame captured by the camera that is being calibrated. In some embodiments, the 3D coordinates may refer to the coordinates of the centers of the components of the jig being imaged. In some embodiments, the 3D coordinates may be obtained from the design and fabrication of the jig. The 2D coordinates may be determined using process 350 as described below.

In step 302, the sets of coordinates may be provided to a calibration algorithm which, in some embodiments, may use direct linear transformation (DLT) to solve the linear equations formed by the projection of the 3D points $(x_i, y_i, z_i)$ to the 2D image coordinates $(u_i, v_i)$:

$$\begin{bmatrix} u_i \\ v_i \\ 1 \end{bmatrix} = P_{3\times 4} \begin{bmatrix} x_i \\ y_i \\ z_i \\ 1 \end{bmatrix} \quad (1)$$

where $P_{3\times 4}$ is the projective transformation matrix (projection matrix) whose components need to be calculated during calibration. This calculation may be done by applying Eq. (1) to at least 6 points to get an equation of the following form:

$$\begin{bmatrix} x_i & y_i & z_i & 1 & 0 & 0 & 0 & 0 & -u_i x_i & -u_i y_i & -u_i z_i & -u_i \\ 0 & 0 & 0 & 0 & x_i & y_i & z_i & 1 & -v_i x_i & -v_i y_i & -v_i z_i & -v_i \\ & & & & & \vdots & & & & & & \end{bmatrix} \begin{bmatrix} P_{00} \\ P_{01} \\ P_{02} \\ P_{03} \\ P_{10} \\ P_{11} \\ P_{12} \\ P_{13} \\ P_{20} \\ P_{21} \\ P_{22} \\ P_{23} \end{bmatrix} = \begin{bmatrix} \vdots \\ 0 \\ 0 \\ \vdots \end{bmatrix} \quad (2)$$

which has the form m=0. Provided that has at least 12 rows that result from at least 6 corresponding 3D and 2D points, Eq. (2) may be solved for all the elements of the projection matrix. In some embodiments, this solving may be done using Singular Value Decomposition (SVD).

In step 304, the projection matrix may be decomposed into the intrinsic and extrinsic parameter matrices for the X-ray camera and the captured images. The projection matrix is formed by the multiplication of the intrinsic and extrinsic parameter matrices. Since the intrinsic parameter matrix is an upper triangular matrix, the projection matrix can be decomposed into the intrinsic and extrinsic parameter matrices outputs of process 300 using a method called RQ-decomposition.

Once the intrinsic and extrinsic parameter matrices have been determined, they may be used for 2D to 3D reconstruction such as described for example in co-owned international patent application PCT/IB2022/053810 to project the 2D images into an initial 3D volume, taking into account the correct projective transformation. The X-ray calibration including determination of the intrinsic and extrinsic parameter matrices as described herein may also be used in a wide variety of scenarios, for example to register a known 3D model to 2D images, to detect 3D landmark points by triangulation of pairs of 2D points detected in multiple 2D images, etc.

In step 306, the 2D coordinates may be detected in an image frame captured by the camera that is being calibrated. The detection algorithm depends on the composition of the jig. In the example of spherical jig components (such as shown in FIGS. 1A-1C), the projections onto 2D images are generally ellipses. In this case circle detection algorithms may be used to find the center and radius of each component. Alternatively, dedicated neural networks (NN) may be used to achieve more stable operation. The result of step 306 yields the 2D coordinates of each component in the image frame captured by the camera that is being calibrated.

The determined 2D components may not be matched to the 3D components, since the first detected component in the 2D image is not necessarily the first 3D jig component, and the ordering may be random since it depends on the projective transformation itself. In step 308, the detected 2D components may be matched to 3D components, i.e., each component i in the 2D frame may be matched to its corresponding component j in the 3D jig design. This again depends on the specific composition of the jig. In some embodiments, for spherical components, different sizes of the spheres can be used to help distinguish between their projections in a hard-coded manner to provide the output 2D image coordinates.

In some embodiments, template matching of the jig may be performed by projecting the 3D design to different simulated 2D projections using different projection parameters, and using these simulated 2D projections to find the best overlap between the imaged and simulated 2D projections. This best overlap may then be used to label the different jig components to provide the output 2D image coordinates.

Figure 4A:
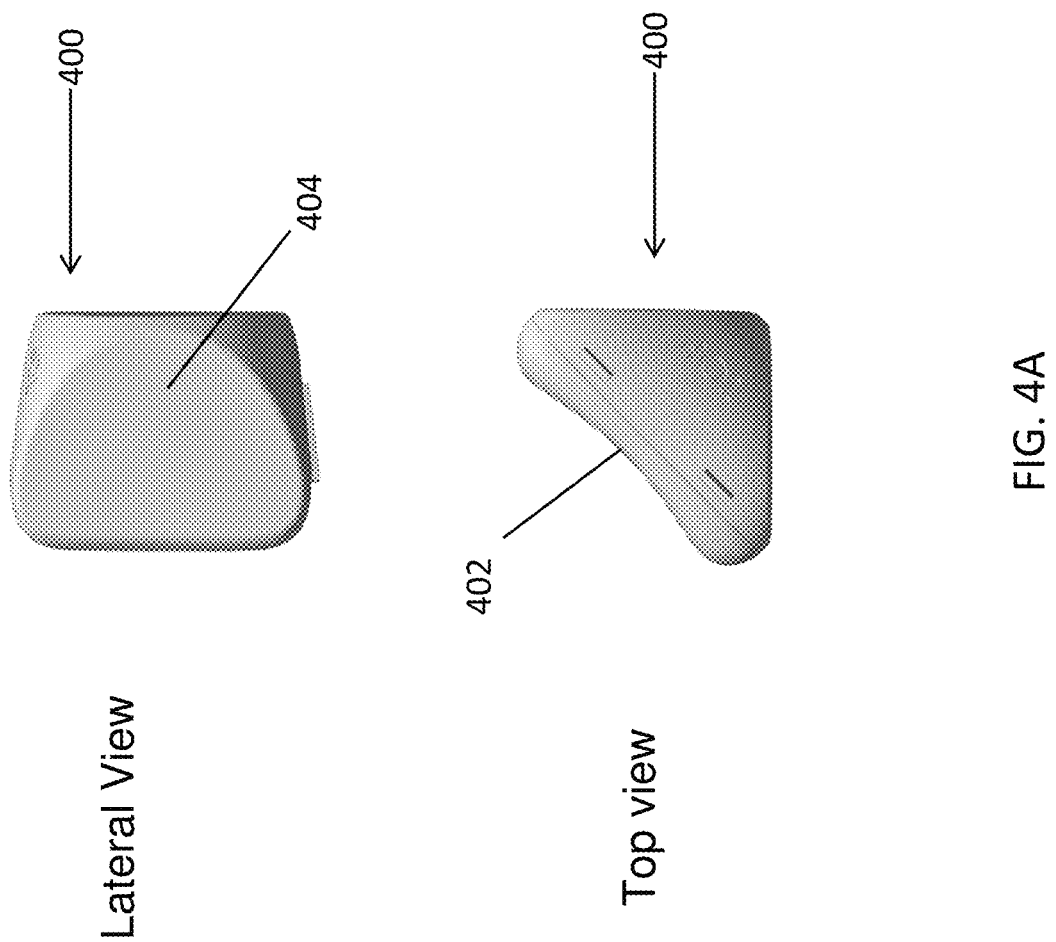
FIG. 4A shows an embodiment of a calibration jig according to some implementations.
Figure 4B:
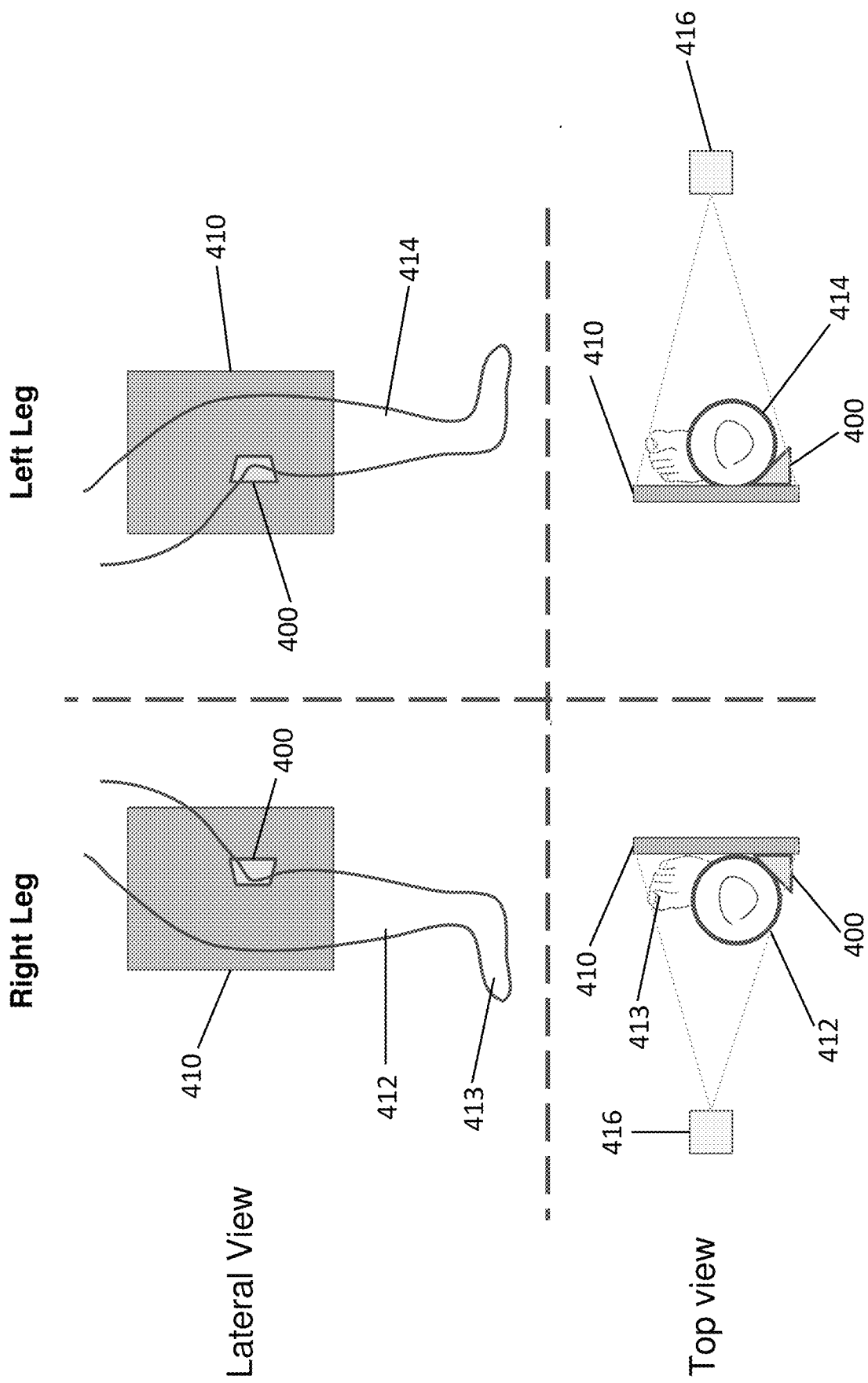
FIGS. 4B and 4C are illustrative drawings showing use of a calibration jig with an X-ray imager according to some implementations.
Figure 4C:
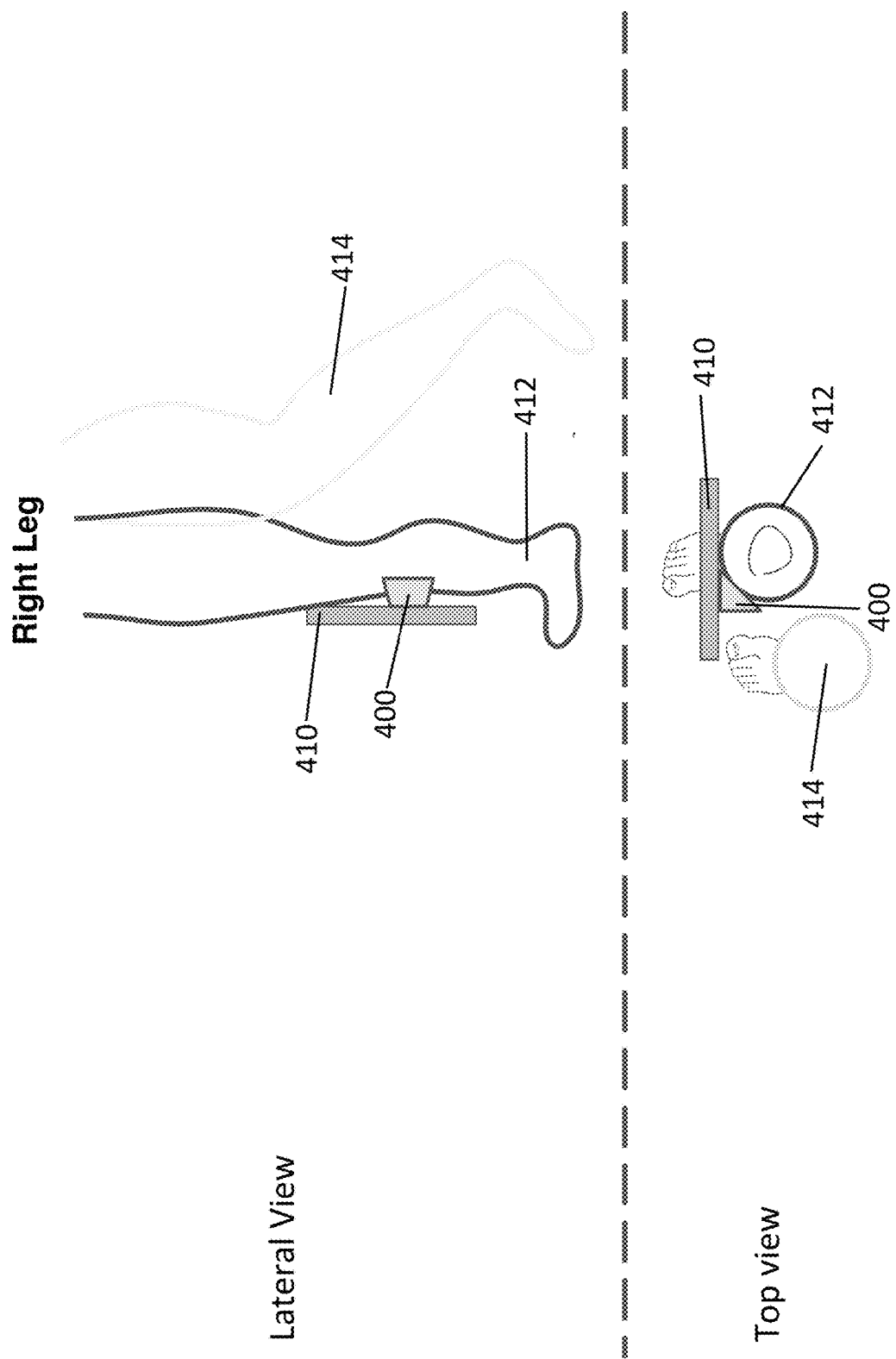

FIG. 4A shows an embodiment of a calibration jig numbered 400 disclosed herein. FIG. 4B is an illustrative drawing shows use of jig 400 with an X-ray imager accordance with embodiments disclosed herein. FIG. 4C an illustrative drawing showing verification of an anatomical position of jig 400 accordance with embodiments disclosed herein. In some embodiments, a series of X-rays of a patient wearing jig 400 may be used to create a 3D reconstruction of bone structures of the patient. In use, jig 400 may be fastened to the patient's legs using a strap (not shown) and then imaged from multiple angles. In some embodiments, two angles may be imaged, including one AP view and one ML view. In the embodiment of FIG. 4B, the primary region of interest to be imaged is the knee joint, namely where the femur and tibia meet.

For use in leg imaging, jig 400 may be formed to provide images with error reduction, to avoid occlusions, and to provide ergonomics and usability. Error reduction (preventing errors and noise in images of the components within jig 400) may be provided by optimized positioning of the components within jig 400 such as by designing jig 400 using process 200. Occlusions between the jig and the subject may lead to a loss of data and potential artifacts, and jig 400 is formed and positioned to avoid occlusions, such as by not covering the knee joint when in position and by optimized positioning of the components therein so that these should not occlude viewing angles covering the bones.

To provide ergonomics and usability, jig 400 may be configured to be comfortable and easily placed, adjustable per patient, and intuitive for a technician to place and align correctly. In some embodiments, jig 400 may have a shape of an isosceles right semi-triangular prism with rounded edges on all sides. In some embodiments, the 45 degree right triangular shape may enable proper alignment of the jig using a perpendicular plane, such as a detector 410, such as shown in FIG. 4B or 4C where one side of the triangular shape is substantially parallel with detector 410. In use, an X-ray technician may use the triangular shape to align the jig to an opposing viewing angle.

A non-limiting example of this alignment aspect is shown in FIG. 4B for right leg 412 and left leg 414 respectively, where the jig is placed at a 45-degree angle on the lateral posterior side of the patient. A non-limiting example of this alignment aspect is shown in FIG. 4C for right leg 412, where the jig is placed at a 45-degree angle on the medial anterior side of the patient. This may allow jig 400 to be placed in a way to guarantee a 45-degree angle on the patient while allowing the patient's leg (412, 414) to also be in contact with detector 410. In some embodiments, the triangular shape of jig 400 may be isosceles to substantially guarantee symmetry on both left and right legs (412, 414) in both AP and ML views relative to a source 416. In some embodiments between capturing the two viewing angles of AP and ML, jig 400 is not moved. The triangular shape may also allow for non-planar organization of the jig components (not shown) with relatively large distances on one axis. With 45-degree positioning (including the anterior-medial position shown in FIG. 4C as well as an alternative posterior-lateral position of FIG. 4B) of any of the jigs described herein, the 45-degree position may help to locate the components (such as components 112) such that they do not occlude the bone in both AP and the ML X-ray images. Foot 413 is shown in FIG. 4B and appears in other similar figures herein.

Jig 400 may have the same structure as jig 100 featuring components enclosed by an enclosure 404. In some embodiments, in order to maximize accuracy and reduce the effect of artifacts, the form of enclosure 404 may be carefully designed in terms of thickness, density, and shape. In some embodiments, enclosure 404 may include rounded edges so as to produce fewer high-intensity artifacts during imaging. In some embodiments, enclosure 404 may be shaped to fit onto an anterior tibial position of a patient. In some embodiments, a vacuum-packed low-density polyethylene may be used to position and hold in place components in a unique 3D arrangement within enclosure 404.

In some embodiments, jig 400 may have a curved inner edge 402 to ergonomically sit on a patient's leg. As used herein "ergonomically sit" or "ergonomically fit" implies that jig 400 is contoured so as to substantially match the shape of and snugly fit against a specific position on a patient's leg and not shift in position when strapped in position. In some embodiments, jig 400 (and also jigs 100, 502, and 600 described herein) may have a curved inner edge 402 (the base of the prism shape) to snugly fit on an anterior medial tibial position of a patient. In some embodiments the posterior-lateral position may be verified by positioning of an isosceles right side of jig 400 against detector 410 such as shown in FIG. 4B. In some embodiments the anterior-medial position may be verified by positioning of an isosceles right side of jig 400 against detector 410 such as shown in FIG. 4C. In some embodiments the posterior-lateral position may be verified by positioning of an isosceles right side of jig 400 as well as the adjacent lateral part of the patient's leg 412 or 414 against detector 410 such as shown in FIG. 4B. In some embodiments the anterior-medial position may be verified by positioning of an isosceles right side of jig 400 as well as the adjacent anterior part of the patient's leg 412 against detector 410 such as shown in FIG. 4C. The snug fit of the curved inner edge 402 may be due to the shape of the curve and due to the fact that the tibia is close to the skin in this area without intervening muscle and the verified anterior-medial placement may thus ensure that the jig will not move relative to the tibia bone even if the patient moves or flexes the leg with the jig attached when moving between the AP and ML X-ray acquisition positions. Is use, jigs 100, 400, 502, and 600 (described below) placed in an anterior-medial tibial position may thus be said herein to provide accurate and stable calibration results due to jig stability relative to the tibia bone. In some embodiments, jig 400 may have an adjustable strap (not shown) that firmly holds the position of jig 400 into place after positioning and/or aligning to a viewing angle.

In some embodiments, a technician's awareness of the positions of the components within enclosure 404 may potentially be useful in avoiding occlusions between the components and the estimated contour of the bones of the patient. For this reason, in some embodiments (since the components may not be visible from the outside of the enclosure), the width of the strap may align with the outermost edge of the components, to hint at the component positions within.

FIGS. 5A-5D show embodiments of a dual calibration jig numbered 500 (herein "dual-jig") in accordance with embodiments disclosed herein. In some embodiments, a series of 2D X-rays of a patient wearing dual-jig 500 may be used to create a 3D reconstruction of bone structures of the patient. In use, dual-jig 500 may be fastened to the patient's legs and then imaged from one or more angles. In some embodiments, only one angle such as AP may be imaged. In other embodiments, two angles may be imaged including one AP view and one ML view. In the embodiment of FIGS. 6A-6D below, two separate jigs 602-1 and 602-2 are used, but it should be appreciated that dual-jig 500 may be optionally used in these examples where the primary region of interest to be imaged is the knee joint.

As shown, dual-jig 500 may include two jigs (here labelled 502-1 and 502-2) that are joined together using a rigid adjustable attachment bar 510 that provides a set of configurable spacing options. In some embodiments, each of jigs 502-1 and 502-2 may be identical to jigs 100 or 400 as described above. In use, if both jigs 502-1, 502-2 are visible within the same view, the connection of multiple jigs together in a known configuration reduces the calibration error by increasing the effective size of the jig. This allows for fixation of the components of the 3D model of interest in the scene between different views to prevent unwanted movements including bending.

On the other hand, if jigs 502-1, 502-2 are too far apart to be seen in the same view, the multiple jigs may be used for another variety of applications. One such application is 2D or 3D stitching. In some embodiments, image stitching may include stitching of an image of the knee joint region to an image of the hip joint region, by imaging dual-jig 500 affixed to an upper portion of the leg (femur region), such that an upper jig 502-1 is close to a hip joint (proximal femur region) and a lower jig 502-2 is close to a knee joint (distal femur region). In some embodiments, image stitching may include stitching of images of the knee joint region to images of the ankle joint region, by imaging dual-jig 500 affixed to a lower portion of the leg (tibia region), such that an upper jig 502-1 is close to a knee joint (proximal tibia region) and a lower jig 502-2 is close to an ankle joint (distal tibia region). In some embodiments, such image stitching of an image of a knee joint region to an image of the hip joint region and/or ankle joint region may be used to determine the mechanical axis or axes of a patient's femur, tibia, and/or whole leg. In 2D, the relative orientation of the images is important in order to combine the images together in a deterministic manner. The preconfigured combination of jigs in dual-jig 500 allows the calculation of this orientation and enables image stitching. In 3D, the reconstruction of multiple segments of the same view can be stitched in a similar manner by calculating the transformations based on the jigs.

Figure 5A:
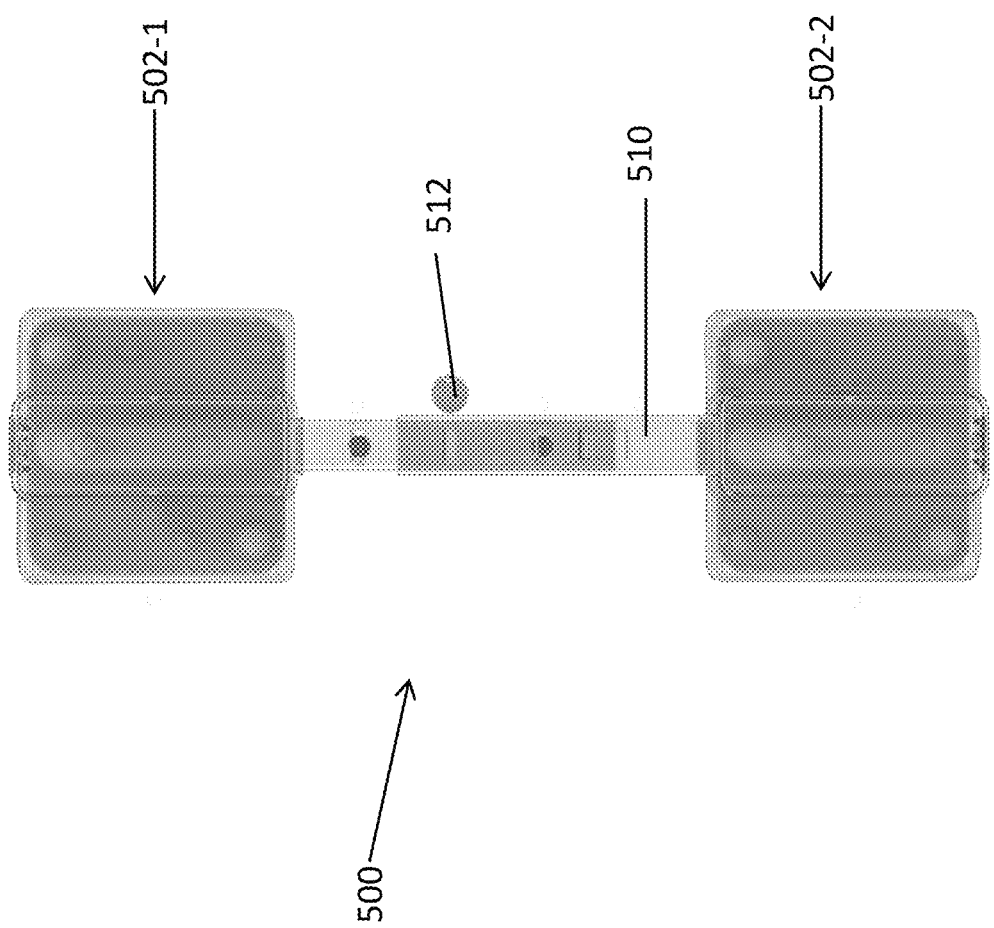
FIGS. 5A-5D show embodiments of a dual calibration jig according to some implementations.
Figure 5D:
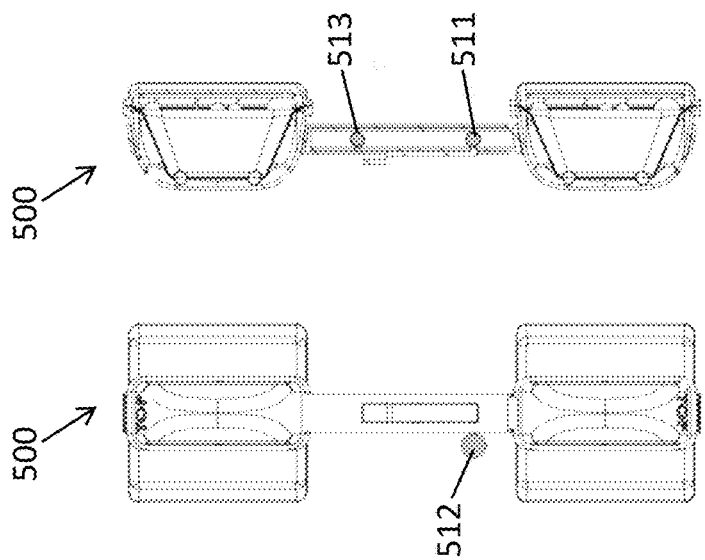
Figure 5C:
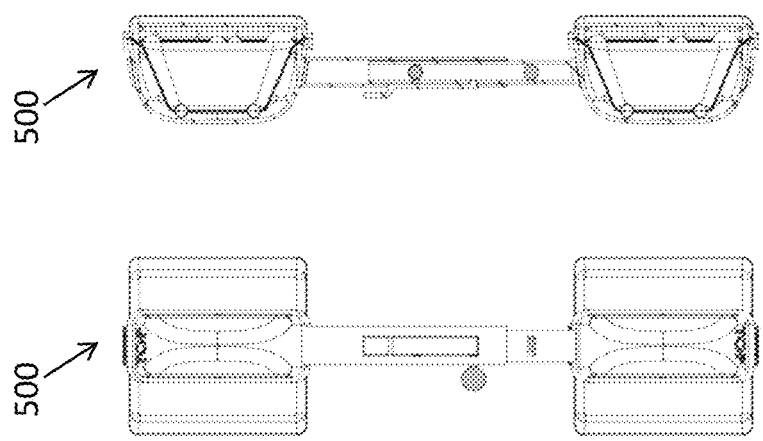
Figure 5B:
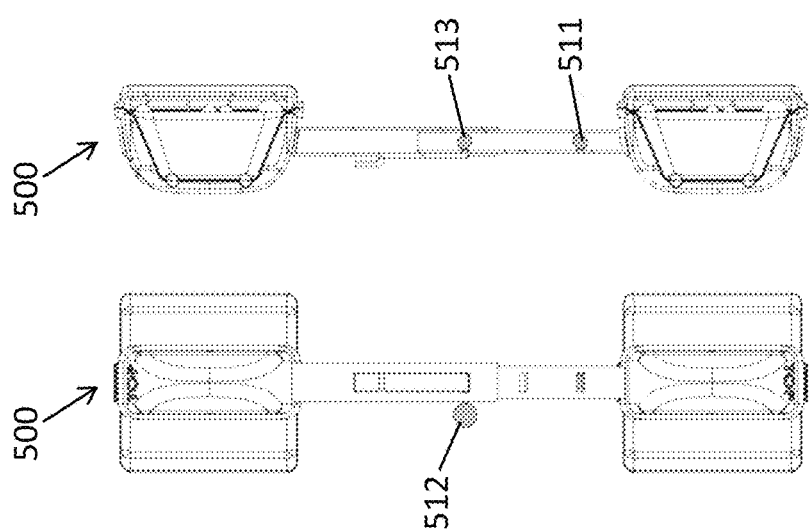

In some embodiments, attachment bar 510 may be pre-configured in one of three different lengths to define the separation between the jigs along its axis. In some embodiments, the jigs are fixed with respect to each other. FIGS. 5B to BD show side and frontal views of three different length configurations of dual-jig 500 from longest to shortest. In some embodiments, bar 510 may include indicator markers 511-513 which may serve to indicate which configuration of the stem is being used. In some embodiments, the largest indicator marker's 512 position with respect to the other two markers 511 and 513 may indicate which configuration is being used. In some embodiments, when the largest marker 512 is aligned to the top small marker 513, bar 510 may be the longest, as shown in FIG. 5B. In some embodiments, when the largest marker 512 is aligned to the bottom small marker 511, bar 510 may be the shortest, as shown in FIG. 5D. In some embodiments, in the remaining configuration the largest marker may be in between the two smaller markers 511 and 513, as shown in FIG. 5C.

For use in leg imaging, dual-jig 500 may be formed to provide images with error reduction, to avoid occlusions, and to provide ergonomics and usability. Error reduction (preventing errors and noise in images of the components within dual-jig 500) may be provided by optimized positioning of the components within jigs 502-1 and 502-2 such as by designing jigs 502-1 and 502-2 using process 200. Occlusions between dual-jig 500 and the subject may lead to a loss of data and potential artifacts, and dual-jig 500 is formed and positioned to avoid occlusions, such as by not covering the knee joint when in position, and by optimized positioning of the components therein so that these should not occlude viewing angles covering the bones.

To provide ergonomics & usability, dual-jig 500 may be configured to be comfortable and easily placed, adjustable per patient, and intuitive for a technician to place correctly and align. As above, in some embodiments each of jigs 502-1 and 502-2 may have a shape and other characteristics of jigs 100 or 400 described above. In some embodiments, a technician's awareness of the positions of the components within the enclosures of jigs 502 may potentially be useful in avoiding occlusions between the components and the estimated contour of the bones of the patient. For this reason, in some embodiments the width of a strap (not shown) used to attach jigs 502 to the patient may align with the outermost edge of the components, to hint at the component positions within.

Figure 6A:
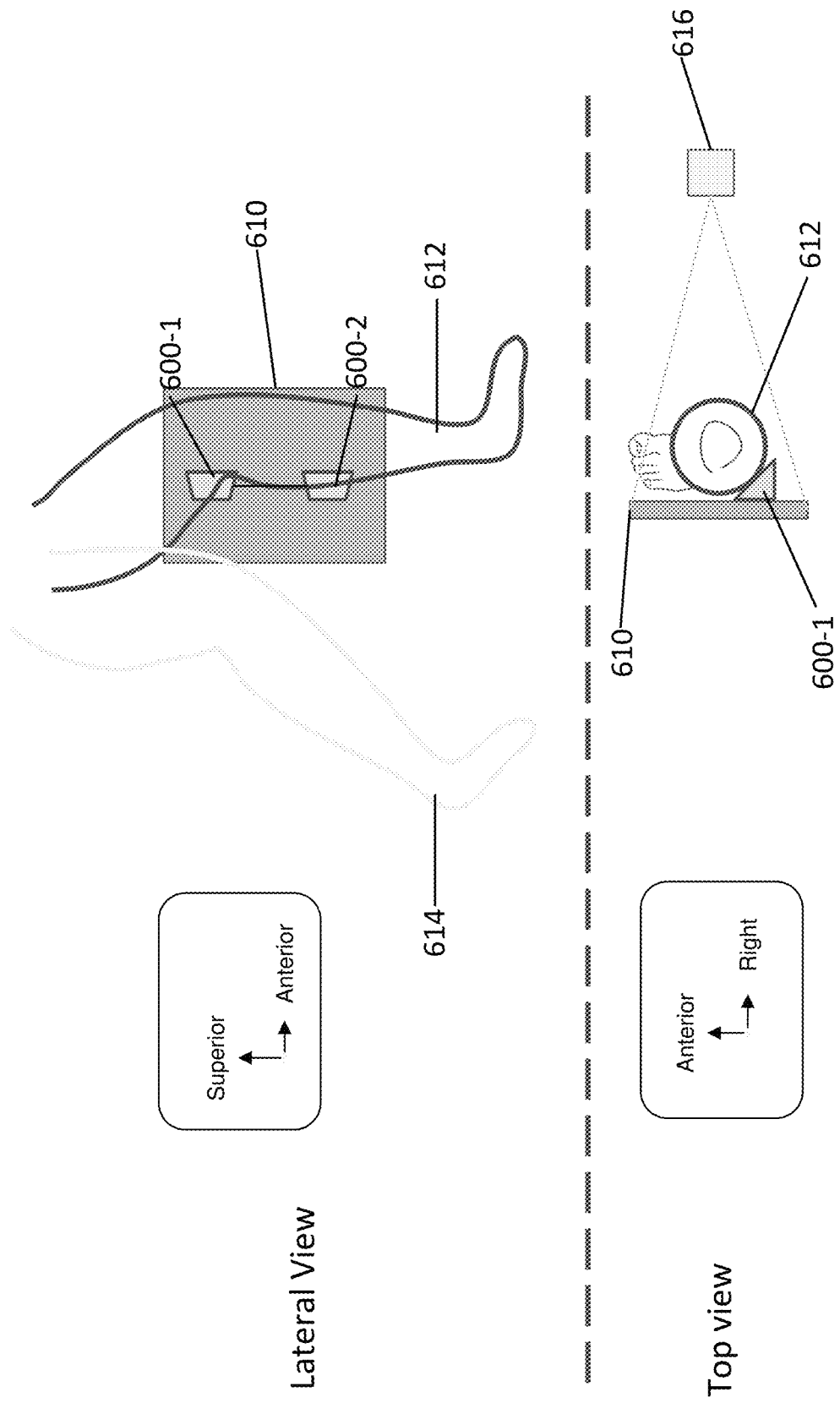
Figure 6B:
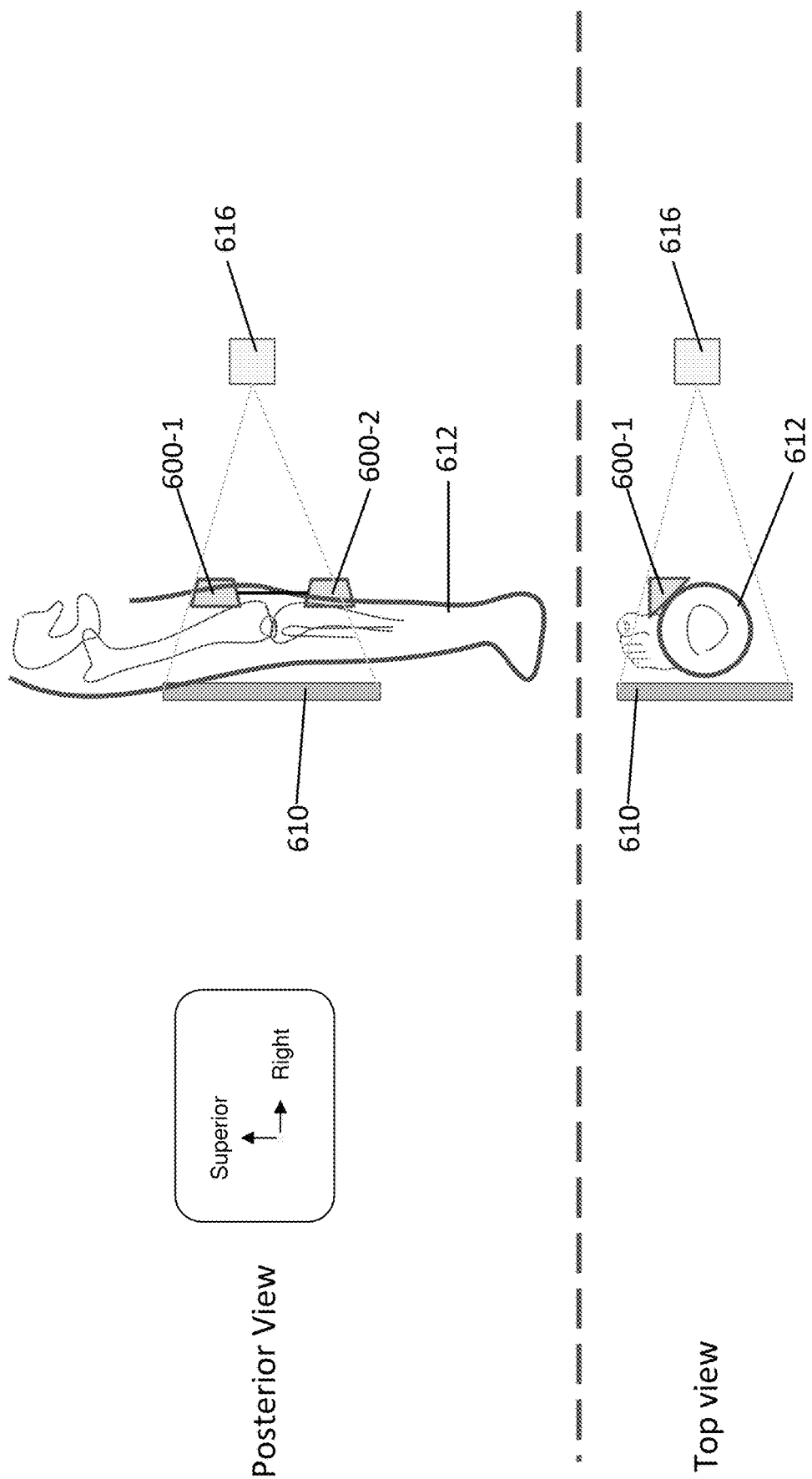
Figure 6C:
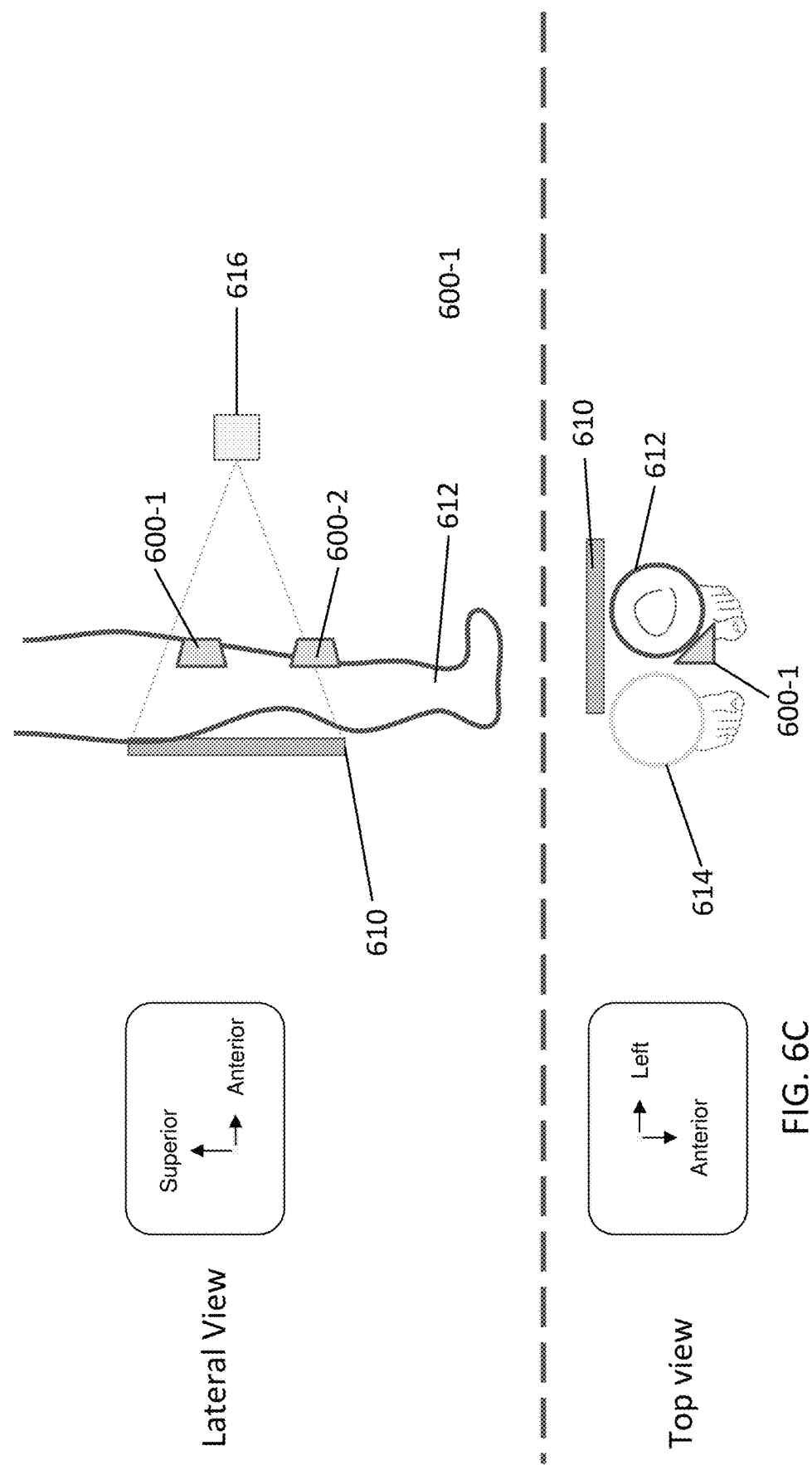

FIGS. 6A-6D show exemplary placement of calibration jigs numbered 600 and the general setup within an imager in accordance with embodiments disclosed herein. FIGS. 6A and 6B show jig placement for ML imaging, and FIGS. 6C and 6D show jig placement for AP imaging. FIGS. 6A and 6D show lateral-posterior placement, and FIGS. 6B and 6C show medial-anterior placement of jigs 600. The exemplary jig placement is shown for ML and AP views of a left leg 612, but it should be appreciated that similar jig positioning may apply for imaging of a right leg 614.

For an ML image (FIGS. 6A and 6B) a detector 610 may be placed laterally with the leg to be imaged (in this case left leg 612 directly in front of it. The source 616 may be placed on the medial side. In some embodiments, for applications of interest, two jigs 600-1 and 600-2, for example, may be fastened to leg 612, one in a femoral position and another in a tibial position. Jigs 600 may be placed in different positions relative to leg 612. Two exemplary positions are shown in FIGS. 6A and 6B, with jigs 600 placed at 45 degrees at the lateral-posterior and medial-anterior corners respectively. The benefit of these two positions is that the distance of jig 600 to detector 610 is consistent between the AP and ML views.

FIGS. 6C and 6D shows exemplary jig placement and the general setup for an AP view of left leg 612. As above, similar considerations may apply for right leg 614. The anatomy, jigs 600, and the X-ray imaging setup are displayed from the lateral, anterior and top views. For an AP image the detector 610 may be placed posteriorly with leg 612 of interest directly in front of it. Source 616 may be placed on the anterior side.

To provide ergonomics and usability, jigs 600 may be configured to be comfortable and easily placed, adjustable per patient, and intuitive for a technician to place correctly and align. In some embodiments, each of jigs 600-1 and 600-2 may have a shape and other characteristics of jigs 100 or 400 as described above. In some embodiments, jigs 600 may be connected by a flexible connector (not shown) to help substantially vertically align jigs 600.

Figure 6E:
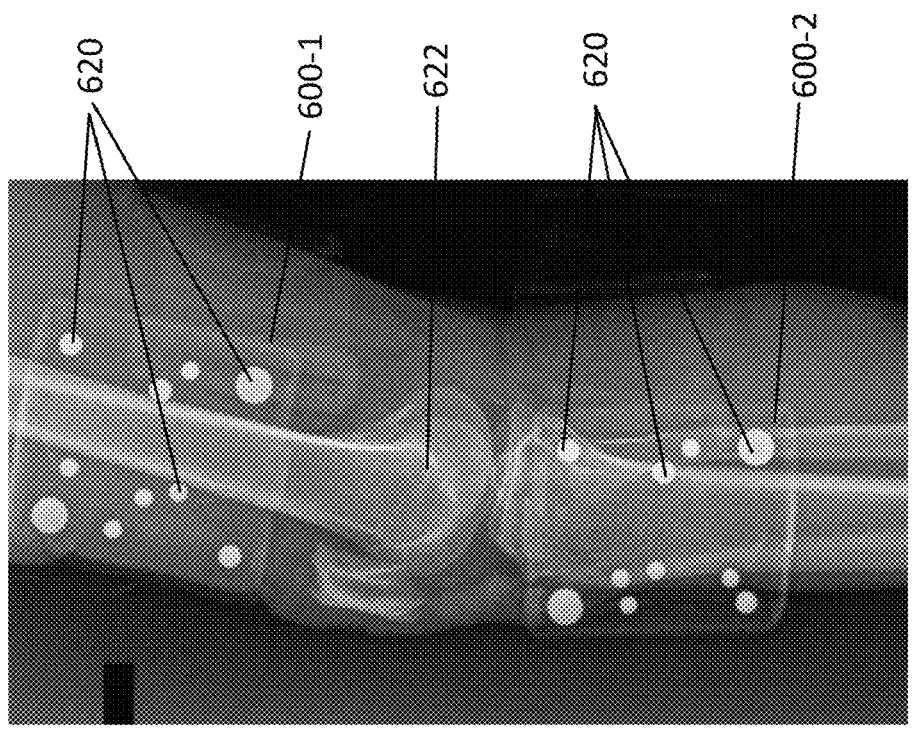
FIG. 6E shows exemplary X-ray images of two calibration jigs in position on a patient according to some implementations.
Figure 6E:
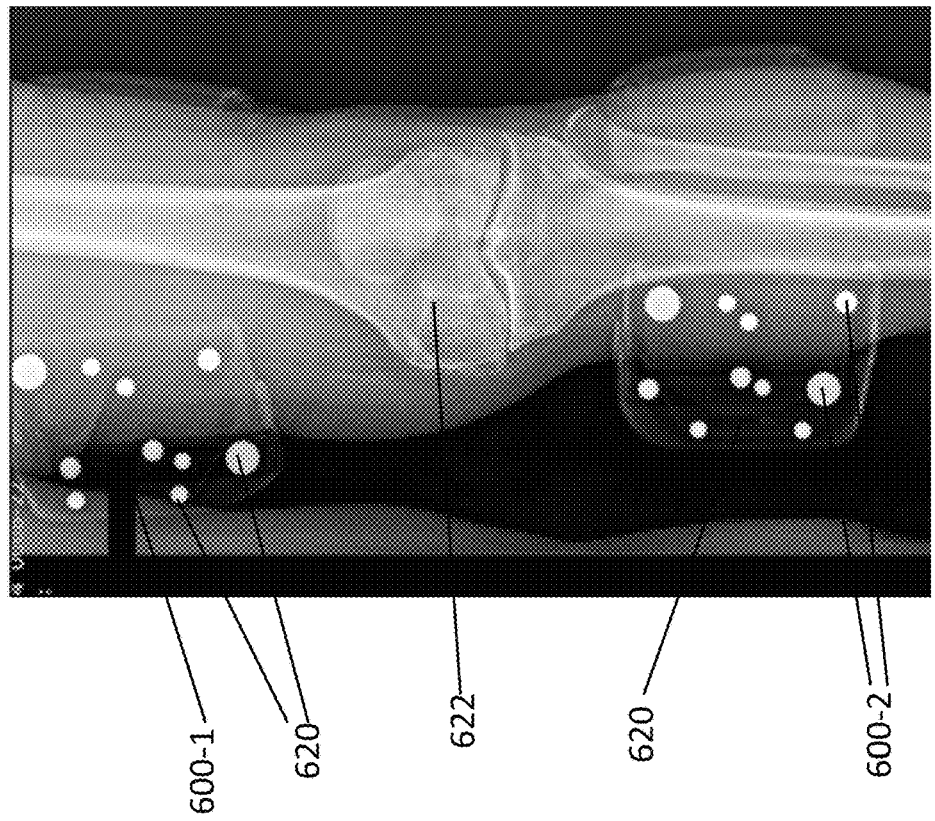

FIG. 6E shows exemplary X-ray images of jigs 600 in position on a patient according to some implementations. In FIG. 6E, the enclosures of jigs 600 are somewhat visible, as well components 620 therein. It should be appreciated that, as shown, components 620 do not overlap and also do not obscure the bones 622 of the patient's knee in both captured views.

Figure 7:
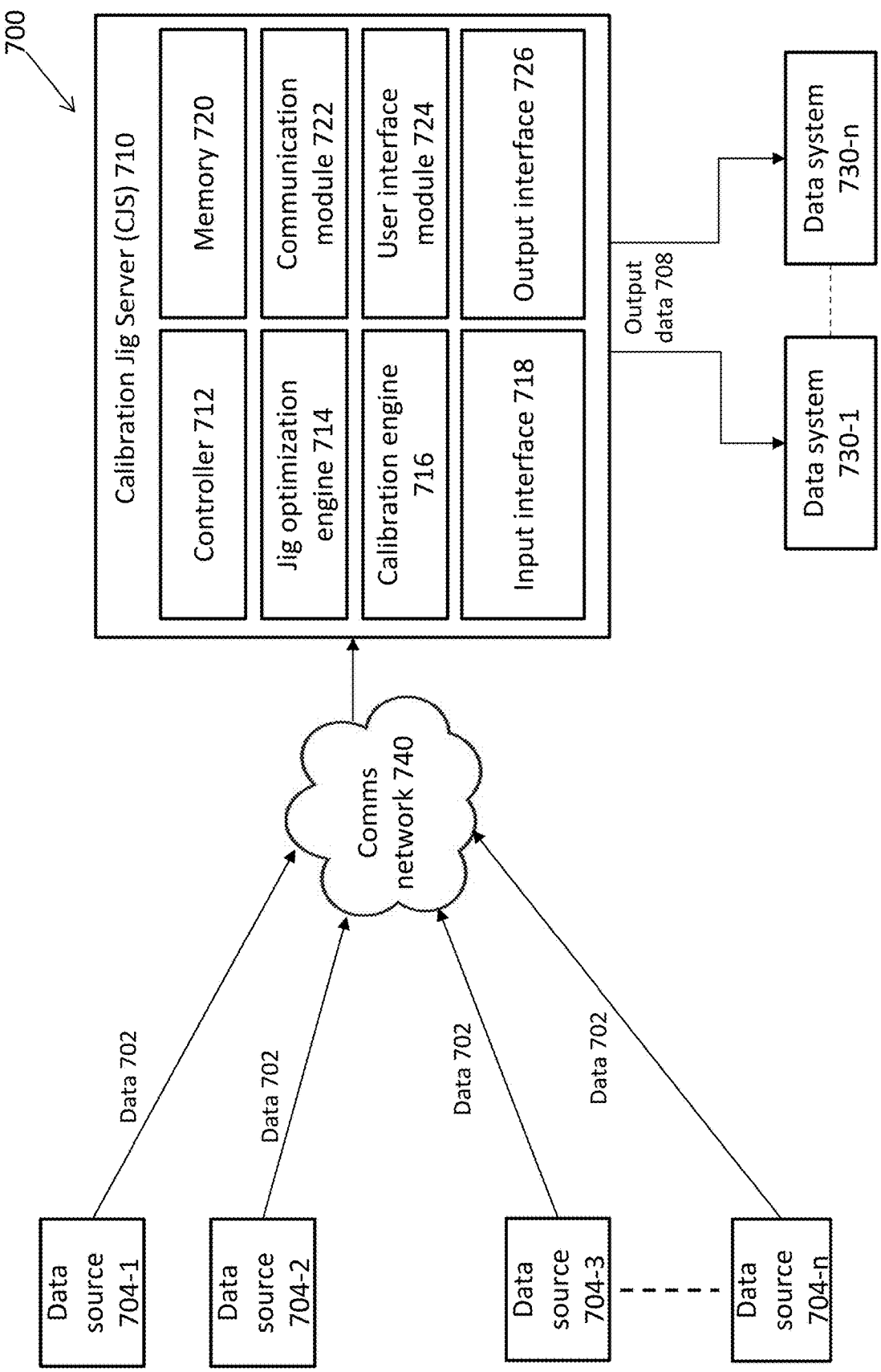
FIG. 7 shows a system for optimization and use of image calibration jigs according to some implementations.

FIG. 7 shows a system numbered 700 for optimization and use of image calibration jigs in accordance with embodiments disclosed herein. As shown in FIG. 7, calibration jig system 700 may include a calibration jig server (CJS) 710 configured to design optimized calibration jigs and to analyze such calibration jigs in use. Calibration jig system 700 may be used with jigs such as jigs 100, 400, 500 and 600 described herein.

In some embodiments, data 702 may be provided from data sources 704 to CJS 710 for use or optimization of jigs. Data sources 704 may include cameras such as X-ray cameras used to capture 2D images. Data 702 may include, for example, inputs provided for processes 200, 300 and 350. In some embodiments, varying types and numbers of data sources 704 (shown in FIG. 7 as data source 704-7, 704-2, 704-3 . . . 704-n) may provide data 702. Data 702 may include training datasets used in machine learning processes.

In some embodiments, data sources 704 may be in data communication with CJS 770 via communications network 740. Communications network 740 may include a wide variety of network configurations and protocols that facilitate the intercommunication of computing devices.

CJS 710 may be a computing device as defined herein. CJS 710 may be implemented on a computer, server, distributed server, virtual server, cloud-based server, and combinations thereof and may make use of cloud and software as a service (SaaS) processing. CJS 710 and the modules and components that are included in CJS 710 may include or may be in communication with a non-transitory computer readable medium (such as memory 720) containing instructions that when executed by at least one processor (such as controller 712) are configured to perform the functions and/or operations necessary to provide the functionality described herein. While CJS 710 is presented herein with specific components and modules, it should be understood by one skilled in the art, that the architectural configuration of CJS 710 as shown may be simply one possible configuration and that other configurations with more or fewer components are possible. As referred to herein, the "components" of CJS 710 may include one or more of the modules or services shown in FIG. 7 as being included within CJS 710.

CJS 710 may include a controller 712. Controller 712 may manage the operation of the components of CJS 710 and may direct the flow of data between the components of CJS 710. Where CJS 710 may be said herein to provide specific functionality or perform actions, it should be understood that the functionality or actions are performed by controller 712 that may call on other components of CJS 710. Controller 712 may be implemented by various types of processor devices and/or processor architectures including, for example, embedded processors, communication processors, graphics processing unit (GPU), soft-core processors and/or embedded processors. In some embodiments, CJS 710 may include memory 720 that may include instructions which, when executed by controller 712 may cause the execution of a method or process described herein.

CJS 710 may include a jig optimization engine 714 and a calibration engine 716 for providing methods, processes and/or operations as described above such as processes 200, 300, and 350. The term "engine" as used herein may also relate to and/or include a computer program module and/or a computerized application and/or one or more hardware, software, and/or hybrid hardware/software modules.

In some embodiments, CJS 710 may include one or more input interfaces 718. Input interface 718 may be configured to ingest and format data 702 for use by CJS 710. In some embodiments, CJS 710 may include a configuration management module 718 which may be configured to configure CJS 710 such as, for example, to optimize the results of and/or provide judgmental qualitative and quantitative measures on the operation of CJS 710.

In some embodiments, CJS 710 may include a communication module 722 for enabling the transmission and/or reception of data, optionally over communication network 740. Communication module 722 may include human interface components (not shown) such as a display device for displaying information to a user and input devices such as a touch screen and/or a keyboard and a pointing device (e.g., a mouse or a trackball) by which the user can provide input to CJS 710.

In use, CJS 710 may provide output data 708 such as from processes 200, 300, and 350. In some embodiments, output data 708 may be provided to one or more data systems 730 (shown in FIG. 7 as data systems 730-1, 730-2). Data systems 730 may include computing devices as defined herein. In some embodiments, output data 708 may be provided to data systems 730 using a variety of output interfaces 726.

Unless otherwise defined, all technical and scientific terms used herein have the same meaning as commonly understood by one of ordinary skill in the art. The materials, methods, and examples provided herein are illustrative only and not intended to be limiting.

Implementation of methods disclosed herein may involve performing or completing certain selected tasks or steps manually, automatically, or a combination thereof. Moreover, according to actual instrumentation and equipment, several selected steps may be implemented by hardware (HW) or by software (SW) on any operating system of any firmware, or by a combination thereof. For example, as hardware, selected steps could be implemented as a chip or a circuit. As software or algorithm, selected steps could be implemented as a plurality of software instructions being executed by a computer using any suitable operating system. In any case, selected steps could be described as being performed by a data processor, such as a computing device for executing a plurality of instructions.

Although the disclosure refers to a "computing device", a "computer", or "mobile device", it should be noted that optionally any device featuring a data processor and the ability to execute one or more instructions may be described as a computing device, including but not limited to any type of personal computer (PC), a server, a distributed server, a virtual server, a cloud computing platform, a cellular telephone, an IP telephone, a smartphone, a smart watch or a PDA (personal digital assistant). Any two or more of such devices in communication with each other may form a "network" or a "computer network".

To provide for interaction with a user, the systems and techniques described here can be implemented on a computer having a display device (a LED (light-emitting diode), or OLED (organic LED), or LCD (liquid crystal display) monitor/screen) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.t In some embodiments, a system disclosed herein may be implemented on one or more servers or storage systems and/or services associated with a business or corporate entity, including for example, a file hosting service, cloud storage service, a hardware server, a virtual server, an online file storage provider, a peer-to-peer file storage or hosting service and/or a cyber locker. In some embodiments, the system disclosed herein may be provided in various deployments models including but not limited to cloud based, hardware server, or virtual.

Memory may include one or more types of computer-readable storage media including, for example, transactional memory and/or long-term storage memory facilities and may function as file storage, document storage, program storage, and/or as a working memory. The latter may, for example, be in the form of a static random-access memory (SRAM), dynamic random-access memory (DRAM), read-only memory (ROM), cache or flash memory. As long-term memory, memory may, for example, include a volatile or non-volatile computer storage medium, a hard disk drive, a solid-state drive, a magnetic storage medium, a flash memory and/or other storage facility. A hardware memory facility may, for example, store a fixed information set (e.g., software code) including, but not limited to, a file, program, application, source code, object code and the like.

As used herein the terms "machine learning" or "artificial intelligence" refer to use of algorithms on a computing device that parse data, learn from the data, and then make a determination or generate data, where the determination or generated data is not deterministically replicable (such as with deterministically oriented software as known in the art). In some embodiments, machine learning algorithms (also referred to herein as machine learning models or artificial intelligence) may be trained using training examples. Further, in some examples, training machine learning algorithms using the training examples may generate a trained machine learning algorithm, and the trained machine learning algorithm may be used to estimate outputs for inputs not included in the training examples. In some examples, a machine learning algorithm may have parameters and hyper parameters.

While certain steps methods are outlined herein as being executed by a specific module and other steps by another module, this should by no means be construed limiting.

It should be understood that where the claims or specification refer to "a" or "an" element, such reference is not to be construed as there being only one of that element. In the description and claims of the present application, each of the verbs, "comprise" "include" and "have", and conjugates thereof, are used to indicate that the object or objects of the verb are not necessarily a complete listing of components, elements or parts of the subject or subjects of the verb.

As used herein, directional terms such as "top," "bottom," "over," "under," "upper," "upward," "lower," "down," and "downward" are intended to provide relative positions for purposes of description, and are not intended to designate an absolute frame of reference or to limit the scope of the embodiments.

While this disclosure has been described in terms of certain embodiments and generally associated methods, alterations and permutations of the embodiments and methods will be apparent to those skilled in the art. The disclosure is to be understood as not limited by the specific embodiments described herein, but only by the scope of the appended claims.

What is claimed is:

1. A method for capturing an X-ray image of a patient's leg comprising:
   attaching a first calibration jig to the patient's leg in an anterior-medial tibial or posterior-lateral tibial position, wherein the first calibration jig has an isosceles right semi-triangular prism shape; and
   verifying that the first calibration jig is in the anterior-medial tibial or posterior-lateral tibial position for the capturing of an X-ray image, wherein the verifying includes positioning an isosceles right side of the first calibration jig against a detector of a device used for the capturing of the X-ray image.

2. The method of claim 1, further comprising capturing an X-ray image in an anterior-posterior (AP) projection and an X-ray image in a lateral projection.

3. The method of claim 1, wherein a base of the semi-triangular prism is curved to ergonomically fit against the patient's leg.

4. The method of claim 1, wherein a base of the semi-triangular prism is curved to ergonomically fit an anterior-medial tibial position on the patient's leg.

5. The method of claim 1, wherein the first calibration jig includes an enclosure and a plurality of components housed inside the enclosure.

6. The method of claim 5, wherein a positioning of the components within the enclosure is optimized to minimise an error metric selected from the group consisting of a reprojection error, an overlap error, and a 3D Euclidean distance error.

7. The method of claim 5, wherein the components include spheres having different radii.

8. The method of claim 5, further comprising:
   providing 2D X-ray images of the first calibration jig attached to the patient's leg, wherein the components have known 3D coordinates within the first calibration jig;
   determining a projection matrix from a projection of the known 3D coordinates to 2D image coordinates of the components captured in the 2D X-ray images; and
   decomposing the projection matrix into intrinsic and extrinsic parameter matrices and using the intrinsic and extrinsic parameter matrices for 3D reconstruction from the 2D X-ray images, wherein the extrinsic parameters relate to the position and rotation of an X-ray camera that captured the 2D X-ray images in relation to the 3D coordinates, and wherein the intrinsic parameters define internal parameters of the X-ray camera.

9. The method of claim 1, further comprising positioning a second calibration jig in a femoral position on the patient's leg.

10. A calibration jig, comprising:

an enclosure;

a plurality of components housed inside the enclosure, and a rigid adjustable attachment bar attached to the calibration jig and to a secondary calibration jig having the same shape as the calibration jig, wherein the enclosure has an isosceles right semi-triangular prism shape, and wherein the calibration jig is configured to be imaged by an X-ray imager.

11. The calibration jig of claim 10, wherein a base of the semi-triangular prism is curved to ergonomically fit against a patient's leg.

12. The calibration jig of claim 10, wherein a base of the semi-triangular prism is curved to ergonomically fit an anterior-medial tibial position on a patient's leg.

13. The calibration jig of claim 10, wherein the components are not radio-opaque.

14. The calibration jig of claim 10, wherein the components are held in fixed positions within the enclosure.

* * * * *